(12) United States Patent
Chang et al.

(10) Patent No.: US 8,928,484 B2
(45) Date of Patent: Jan. 6, 2015

(54) SYSTEM AND METHOD OF BIOMECHANICAL POSTURE DETECTION AND FEEDBACK

(75) Inventors: Andrew Robert Chang, Sunnyvale, CA (US); Monisha Perkash, Los Altos Hills, CA (US); C. Charles Wang, Palo Alto, CA (US); Andreas Martin Hauenstein, San Mateo, CA (US)

(73) Assignee: Lumo Bodytech, Inc., Palo Alto, CA (US)

( * ) Notice: Subject to any disclaimer, the term of this patent is extended or adjusted under 35 U.S.C. 154(b) by 294 days.

(21) Appl. No.: 13/548,093

(22) Filed: Jul. 12, 2012

(65) Prior Publication Data

US 2013/0015976 A1  Jan. 17, 2013

Related U.S. Application Data

(60) Provisional application No. 61/507,514, filed on Jul. 13, 2011, provisional application No. 61/547,590, filed on Oct. 14, 2011.

(51) Int. Cl.
| | | |
|---|---|---|
| *G08B 23/00* | (2006.01) | |
| *A61B 5/00* | (2006.01) | |
| *A61B 5/11* | (2006.01) | |
| *A61B 5/06* | (2006.01) | |

(52) U.S. Cl.
CPC ............. *A61B 5/0002* (2013.01); *A61B 5/1116* (2013.01); *A61B 5/1121* (2013.01); *A61B 5/4561* (2013.01); *A61B 5/486* (2013.01); *A61B 5/067* (2013.01); *A61B 5/6823* (2013.01)
USPC .................................. 340/573.7; 340/573.1

(58) Field of Classification Search
CPC .. A61B 5/1116; A61B 5/103; G08B 21/0438; G08B 21/0446
USPC ....................................................... 340/573.7
See application file for complete search history.

(56) References Cited

U.S. PATENT DOCUMENTS

| | | |
|---|---|---|
| 4,633,094 A | 12/1986 | Knudsen |
| 5,143,088 A | 9/1992 | Marras et al. |
| 5,158,089 A | 10/1992 | Swezey et al. |
| 5,388,591 A | 2/1995 | De Luca et al. |
| 5,398,697 A | 3/1995 | Spielman |
| 5,749,838 A | 5/1998 | Kline |
| 5,916,181 A | 6/1999 | Socci et al. |
| 5,919,149 A | 7/1999 | Allum |
| 6,032,530 A | 3/2000 | Hock |
| 7,264,554 B2 | 9/2007 | Bentley |

(Continued)

OTHER PUBLICATIONS

Unknown, "Accelerometer", in Wikipedia (archived Apr. 1, 2011 at http://web.archive.org/web/20110401205940/http://en.wikipedia.org/wiki/Accelerometer), pp. 1-21.

(Continued)

*Primary Examiner* — Kerri McNally
(74) *Attorney, Agent, or Firm* — Gard & Kaslow LLP

(57) ABSTRACT

A system and method are described herein for a sensor device which biomechanically detects in real-time a user's movement state and posture and then provides real-time feedback to the user based on the user's real-time posture. The feedback is provided through immediate sensory feedback through the sensor device (e.g., a sound or vibration) as well as through an avatar within an associated application with which the sensor device communicates.

6 Claims, 14 Drawing Sheets

(56) References Cited

U.S. PATENT DOCUMENTS

| | | | |
|---|---|---|---|
| 7,431,703 | B2 | 10/2008 | Salvi et al. |
| 7,602,301 | B1* | 10/2009 | Stirling et al. ............. 340/573.1 |
| 7,634,379 | B2 | 12/2009 | Noble |
| 7,698,830 | B2 | 4/2010 | Townsend et al. |
| 2005/0126026 | A1 | 6/2005 | Townsend et al. |
| 2007/0015611 | A1 | 1/2007 | Noble et al. |
| 2007/0167671 | A1 | 7/2007 | Miller, III |
| 2008/0319352 | A1 | 12/2008 | Chow et al. |
| 2010/0205541 | A1 | 8/2010 | Rapaport et al. |
| 2010/0298655 | A1* | 11/2010 | McCombie et al. .......... 600/301 |
| 2010/0312152 | A1 | 12/2010 | Sarkodie-Gyan et al. |
| 2011/0063114 | A1 | 3/2011 | Ikoyan |

OTHER PUBLICATIONS

Unknown, "Back Pain", in Wikipedia (archived Feb. 25, 2011 at http://web.archive.org/web/20110225132125/http://en.wikipedia.org/wiki/Back_pain), pp. 1-22.

Unknown, "Mahalanobis Distance", in Wikipedia (archived Mar. 29, 2010 at http://web.archive.org/web/20100329232341/http://en.wikipedia.org/wiki/Mahalanobis_distance), pp. 1-8.

Unknown, "Neutral Spine", in Wikipedia (archived Feb. 12, 2011 at http://web.archive.org/web/20110212145135/http://en.wikipedia.org/wiki/Neutral_spine), pp, 1-7.

Unknown, "Rotation", in Wikipedia (archived Mar. 31. 2011 at http://web.archive.org/web/20110331232736/http://en.wikipedia.org/wiki/Rotation), pp. 1-13.

Patel. A.T. and Ogle, Abna A. (2000), "Diagnosis and Management of Acute Low Back Pain", in American Family Physician 15:61(6) (accessible at http://www.aafp.org/afp/2000/0315/p1779.html), pp. 1779-1786.

Unknown (2000), "Information from Your Family Doctor: Acute Low Back Pain", in American Family Physician 15:51(6) (accessible at http://www.aafp.org/afp/2000/0315/p1789.html), pp. 1-4.

Unknown, "A Patient's Guide to Rehabilitation for Low Back Pain", University of Maryland Spine Program (archived Jun. 7, 2011 at http://web.archive.org/web/20110607181952/http://www.umm.edu/spinecenter/education/rehabilitation_for_low_back_pain.htm), pp. 1-10.

Clifford, Michelle and Gomez, Leticia (2005), "Measuring Tilt with Low-g Accelerometers", in Freescale Semiconductor Application Note, (accessible at http://www.freescale.com/files/sensors/doc/app_note/AN3107.pdf), pp. 1-8.

Kesson, Malcolm (2002), "Mel: Align Y Axis to Vector", in CG References & Tutorials at Fundza.com (accessible at http://www.fundza.com/mel/axis_to_vector/align_axis_to_vector.html), pp. 1-6.

Unknown, "Sensors", at freescale.com (accessed May 14, 2012 at http://www.freescale.com/webapp/sps/site/homepage.jsp?nodel=011269), pp. 1-2.

* cited by examiner

SYSTEM AND METHOD OF BIOMECHANICAL POSTURE DETECTION AND FEEDBACK

CROSS-REFERENCE TO RELATED APPLICATIONS

This application claims priority of U.S. Provisional Patent Application No. 61/507,514, entitled "Biomechanics Sensory System" and filed Jul. 13, 2011, the disclosure of which is incorporated herein by reference and U.S. Provisional Patent Application No. 61/547,590, entitled "Biomechanical Sensor System and Method" and filed Oct. 14, 2011, the disclosure of which is incorporated herein by reference.

BACKGROUND OF THE INVENTION

1. Field of the Invention

The present invention relates generally to biomechanical sensors used for biofeedback, and in particular, to biomechanical sensors that interface with computing devices.

2. Description of the Prior Art

Inactivity and poor posture can cause significant back problems. About nine out of ten adults experience back pain at some point in their life, and five out of ten working adults have back pain every year. A. T. Patel and A. A. Ogle (2000), "Diagnosis and Management of Acute Low Back Pain", in *American Family Physician*, March 15; 61(6): 1779-1786.

Back pain also exacts a huge economic cost—estimated to be over $50 billion per year in direct (e.g., health care expenditures) and indirect (e.g., lost productivity) costs. In the United States, back pain is the primary reason for job-related disability, one of the leading causes of missed work days, the primary reason for people younger than 45 to limit their activity, and the second most common reason for visits to the doctor.

Medical practitioners agree that back pain can often be reduced by maintaining good posture—that is, a "neutral spine" posture—while sitting, standing, lying, or moving. The neutral spine posture in a healthy spine is an optimal position of three natural curves of the spine: a neck (cervical) region, a mid-back (thoracic) region, and a lower-back (lumbar) region. As shown in FIG. 1, the neck region curve involves cervical vertebrae C1-C7, and is ideally anteriorly convex (i.e., should curve inward). The mid-back region curve involves thoracic vertebrae T1-T12, and is ideally posteriorly convex (i.e., should curve outward). The lower-back region curve involves lumber vertebrae L1-L5 and is ideally anteriorly convex (i.e., should curve inward).

Posture is determined to some degree by pelvic tilt. As shown in diagram 201 of FIG. 2, a neutral pelvis (i.e., a pelvis that is not tilted) indicates that anterior superior iliac spines (ASIS) and the pubic symphysis (not visible in FIG. 2) fall along a vertical line running through the leg bones, the anterior curves of the lumbar and cervical regions, and out the top of the head.

If the ASIS and pubic symphysis are not properly aligned, the pelvis is rotated and thereby changes the curvatures of the lumbar, thoracic, and/or cervical regions of the spine. When the pelvis is rotated to a forward tilting position (i.e., an anteverted position), the lumbar curvature increases beyond a neutral spine position. When this anterior rotation of the pelvis is extreme, it can result in an unhealthy swayback posture (i.e., lordosis) as shown in diagram 202. If an individual instead slouches, the pelvis rotates to a backward tilting position (i.e., a retroverted position as shown in diagram 203), thereby flattening out the cervical, thoracic, and lumbar curvatures as also shown in the figure.

Biofeedback (i.e., a process of using physiological indicators of a biological system to monitor and control behavior of that biological system) is one way to provide feedback to individuals about how their bodies are functioning, with a goal of using that information to monitor and change problematic behaviors, such as smoking and weight gain. As an example, U.S. Pat. No. 5,749,838 (Kline) discloses a posture training device which can be held against the backbone of a person by a belt or garment such that an increase in curvature of the backbone in either a midsagittal or transverse plane moves a module within a frame relative to the frame. When the module has been moved sufficiently to indicate a poor posture position, a tactile signal generator within the module is activated to vibrate, thereby alerting the person that he has assumed a poor posture.

This and other conventional biomechanical devices typically require garments or belts to hold sensors in place. It can be difficult to apply these devices in a way that people find visually appealing, comfortable, and convenient. Furthermore, these devices tend to be bulky, adding to the discomfort of wearing these devices. What is needed is a flexible, comfortable device that can measure a user's positions and movements to provide postural feedback.

SUMMARY

In one embodiment is a method of providing postural feedback comprising: receiving by a microprocessor at repeated intervals data from a tri-axial accelerometer, the microprocessor and the tri-axial accelerometer comprising a sensor device attached to a user, the sensor device further comprising memory, an actuator, and a power source; normalizing by the microprocessor the received accelerometer data; determining by the microprocessor a postural description of the user based on the normalized received accelerometer data; and triggering by the microprocessor the actuator to output sensory feedback based on the postural description of the user.

In another embodiment is a postural feedback apparatus comprising: a sensor device configured to be attached on a user, the sensor device comprising: a tri-axial accelerometer; an actuator; and a microprocessor configured to receive data from the tri-axial accelerometer about movement of the user; normalize the received accelerometer data; determine a postural description of the user based on the normalized received accelerometer data; and trigger the actuator to output sensory feedback based on the postural description of the user.

A non-transitory computer readable medium having stored thereupon computing instructions comprising: a code segment to receive by a microprocessor at repeated intervals data from a tri-axial accelerometer, the microprocessor and the tri-axial accelerometer comprising a sensor device attached to a user, the sensor device further comprising memory, an actuator, and a power source; a code segment to normalize by the microprocessor the received accelerometer data; a code segment to determine by the microprocessor a postural description of the user based on the normalized received accelerometer data; and a code segment to trigger by the microprocessor the actuator to output sensory feedback based on the postural description of the user.

DETAILED DESCRIPTION OF THE INVENTION

Presented herein are various embodiments of a sensor device and methods for using the sensor device that biomechanically detects a user's posture and provides sensory feedback in real-time about the posture to the user. The feedback is provided in real-time through an actuator that provides sensory activity (e.g., vibration or sound) and/or through an avatar within a corresponding application with which the sensor device communicates.

The sensor device itself comprises an accelerometer and a microprocessor that analyzes directional movement data from the accelerometer. When the sensor device is attached to a user, the microprocessor can analyze accelerometer data indicative of a user's motion in real-time to determine a user's movement state (e.g., standing, sitting, lying, running, or walking) and assess the user's posture in that movement state (i.e., a posture quality of the user). Using various models, the microprocessor can rapidly determine a user's movement state directly by identifying a user's movement state or indirectly by identifying transitions ("state transitions") between movement states. Thus, the microprocessor can provide rapid feedback to the user about his/her posture.

Location of the microprocessor on the patch offers advantages over current feedback devices. For example, known feedback devices that communicate wirelessly with feedback display devices (e.g., wristwatches) depend upon the wireless communication in order to make any determinations and provide feedback, and thereby deplete battery power more rapidly than embodiments of the sensor device discussed herein which allow continuous (24 hours a day, 7 days a week) data gathering while minimizing the energy cost of wireless communication. Unlike the sensor device discussed herein, known feedback devices (e.g., the Polar heart monitor by Polar Electro, Finland) use a simple broadcast model to send raw data to be interpreted by a receiving unit. Other known feedback devices perform minimal local processing (e.g., Fitbit, by Fitbit Inc., San. Francisco, Calif. and Lark, by Lark Technologies, Mountain View, Calif.) whereas the sensor device described herein performs local data processing and analysis in real-time.

Figure 3:
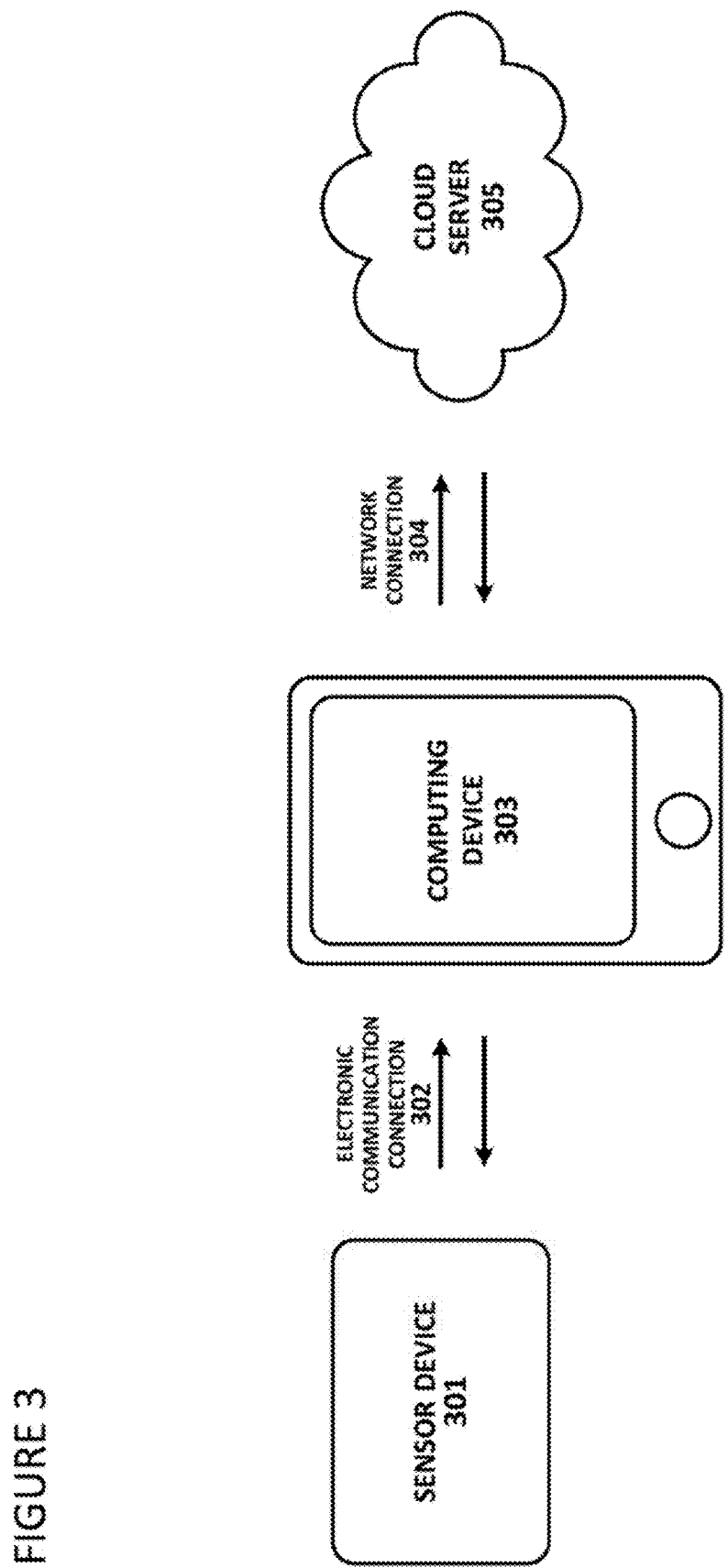
FIG. 3 is a block diagram illustrating a biomechanical posture detection and feedback system according to one embodiment.

A block diagram of the system for biomechanical posture detection and sensory feedback according to one embodiment is presented in FIG. 3. Sensor device 301 senses position and movement data over time for a user (not shown) to whom sensor device 301 is attached, processes and analyzes the position and movement data to determine in real-time a postural description of the user, and stores the position and movement data and postural description in memory. In some embodiments, sensor device 301 transmits the position and movement data and postural description wirelessly through an electronic communication connection 302 to computing device 303 for use by a corresponding application running on computing device 303 is active. Sensor device 301 and/or computing device 303 can also transmit the data and postural description through network connection 304 to a cloud server 305 on which the user may have a personal data hub (discussed in further detail herein).

Computing device 303 is a computing device such as a smartphone (e.g., an iPhone from Apple, Inc., a BlackBerry device from Research in Motion Limited, or a phone running the Android OS from Google, Inc. of Mountain View, Calif.) or any computing device with a user interface such as a phone, personal digital assistant (PDA), media device (such as an iPod or iPod Touch from Apple, Inc.), electronic tablet (such as an iPad from Apple, Inc., or an HP Slate from Hewlett-Packard Development Company, L.P.), an electronic reader device (such as a Kindle or Kindle DX from Amazon.com, Inc. of Seattle, Wash., or The Reader from SONY Electronics Inc.), a laptop computer, or a desktop computer.

One of ordinary skill in the art will understand that electronic communication connection 302 between sensor device 301 and computing device 303 can be, but need not be the same as network 304 between computing device 303 and cloud 304. Electronic communication connection 302 is a wireless computing (e.g., governed by Wi-Fi protocols such as Bluetooth) or telecommunications (e.g., governed by 3 G or 4 G protocols) connection or network. Network 304 can be a wireless or wired network, or a telecommunications connection or network (e.g., governed by 3 G or 4 G protocols). Electronic communication connection 302 and network 304 can each or both be a wide area network (WANs), a local area network (LAN), a global area network (GAN), a virtual private network (VPN), a personal area network (PAN), an enterprise private network, or any similar network now known or later developed.

Figure 4:
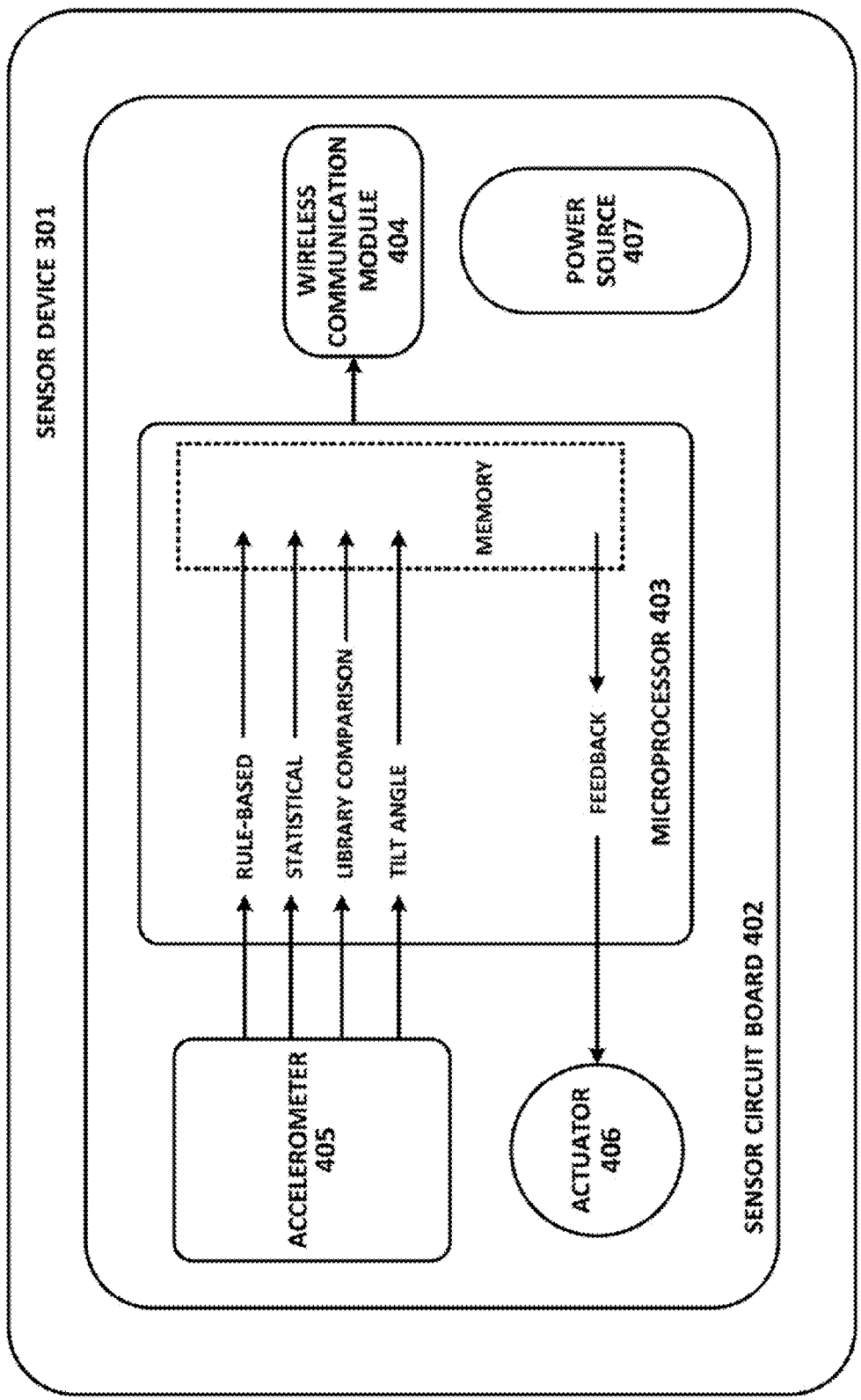
FIG. 4 is a block diagram illustrating a sensor device of a biomechanical posture detection and feedback system according to one embodiment.

Embodiments of sensor device 301 have a variety of form factors. One embodiment of sensor device 301 is shown in the block diagram of FIG. 4. In this embodiment, sensor device 301 comprises a sensor circuit board 402 attached to a pad, which pad is attached to a thin and flexible adhesive. The flexible adhesive can be any removable adhesive that will stick to human skin and/or cloth (e.g., nylon, polyester). In another embodiment, sensor device 301 comprises an attachable or clip-on device in addition to or instead of the flexible adhesive. Such a device (not shown) can be used to attach sensor device 301 to, e.g., a belt, clothing, sports equipment, or a carrying bag. In yet another embodiment, sensor device 301 can be embedded into other form factors such as a belt, a tight-fitting athletic shirt, a band, or underwear.

In one embodiment, sensor circuit board 402 comprises a microprocessor 403 with memory, a wireless communication module 404, an accelerometer 405, an actuator 406, and a power source 407 (e.g., battery) which powers sensor circuit board 402. In other embodiments, the memory (e.g., a memory chip) is external to microprocessor 403. In other embodiments, sensor circuit board 402 does not comprise actuator 406.

Accelerometer 405 is a tri-axial accelerometer configured to measure proper acceleration (i.e., experienced acceleration relative to free-fall) along horizontal (x-), vertical (y-), and transverse (z-)axes. As the user (with sensor device 301 attached) moves, accelerometer 405 captures tri-axial acceleration data (i.e., data along the x-, y-, and z-axes) at, e.g., a 50 Hz sampling frequency. The sampled data are passed to microprocessor 403 for storage and for processing to determine a postural description of the user. A postural description comprises a user's movement state (e.g., standing, sitting, lying, running, or walking) and/or posture quality (i.e., how well the user is balanced within that movement state, e.g., whether and how well the user's posture matches a desirable "good posture" for the determined movement state). Microprocessor 403 then triggers actuator 406 to provide sensory feedback to the user in real-time based on the determined postural description of the user.

Microprocessor 403 is configured for cycling at a given rate, preferably processing accelerometer data at a sample rate of 32 Hz. Microprocessor 403 uses various models discussed herein (e.g., a rule-based model, a statistical model, a library comparison model, and/or a tilt angle model) to analyze accelerometer data in order to determine user movement states and posture quality. Microprocessor 403 is further configured with memory to store data received from accelerometer 405 as well as determined movement and posture quality. Microprocessor 403 is additionally configured to use movement and posture quality to command feedback based on the determined movement states and posture quality to be delivered through actuator 406 and/or through computing device 303 to the user.

Actuator 406 is a feedback delivery apparatus such as a vibratory motor and/or a sound device. In other embodiments, computing device 303 can be an additional feedback delivery apparatus and/or can be used as a feedback delivery apparatus in lieu of actuator 405.

Microprocessor 403 forwards the postural description determinations and/or the accelerometer data, to wireless communication module 404 which in turn communicates wirelessly with a corresponding application on computing device 303 to synchronize the data and postural description information with a user's personal data hub (or profile) stored on computing device 303 or on cloud server 305. Microprocessor 403 also stores the accelerometer data in memory if the sensor device is not in range for communication with computing device 303.

Microprocessor 403 synchronizes through wireless communication module 404 with the application running on computing device 303 and/or with cloud server 305 to upload the user's data and determined movement states. The rapid processing and storage capabilities of microprocessor 403 offer benefits over known feedback devices (e.g., feedback sensors communicating with a user's wristwatch to provide feedback).

Wireless communication module 404 is configured to communicate wirelessly with computing device 303 via a network protocol such as a Bluetooth proprietary open standard (created by Ericsson of Sweden and managed by the Bluetooth Special Interest Group, Kirkland, Wash.), or through a cellular network. Wireless communication module 404 synchronizes user data (e.g., postural descriptions, pelvic tilt angles, determined movement states, state changes, and/or raw accelerometer data) through electronic communication connection 302 with computing device 303 for use by a corresponding application running on computing device 303. Computing device 303 synchronizes user data through network connection 304 with a user's personal hub in cloud server 305.

In other embodiments, one or more additional sensor can be added to sensor device 301 to enhance accuracy of posture and movement detection. Examples include other light weight, very thin and/or unobtrusive microelectrical mechanical system (MEMS)-based sensors. In one embodiment, a MEMS-based gyroscope can be added to sensor device 301 to enhance rotary sensing capability (i.e., ability to detect twisting and bending). In another embodiment, a MEMS-based strain gauge can be used to determine a relational change between the pelvis and the lower back. The relational change alters resistance of the strain gauge, which resistance can be mapped to various states of good and bad posture. In yet another embodiment, MEMS-based electromyogram sensors can be used to detect muscle strain which can be correlated to various states of posture.

Figure 5:
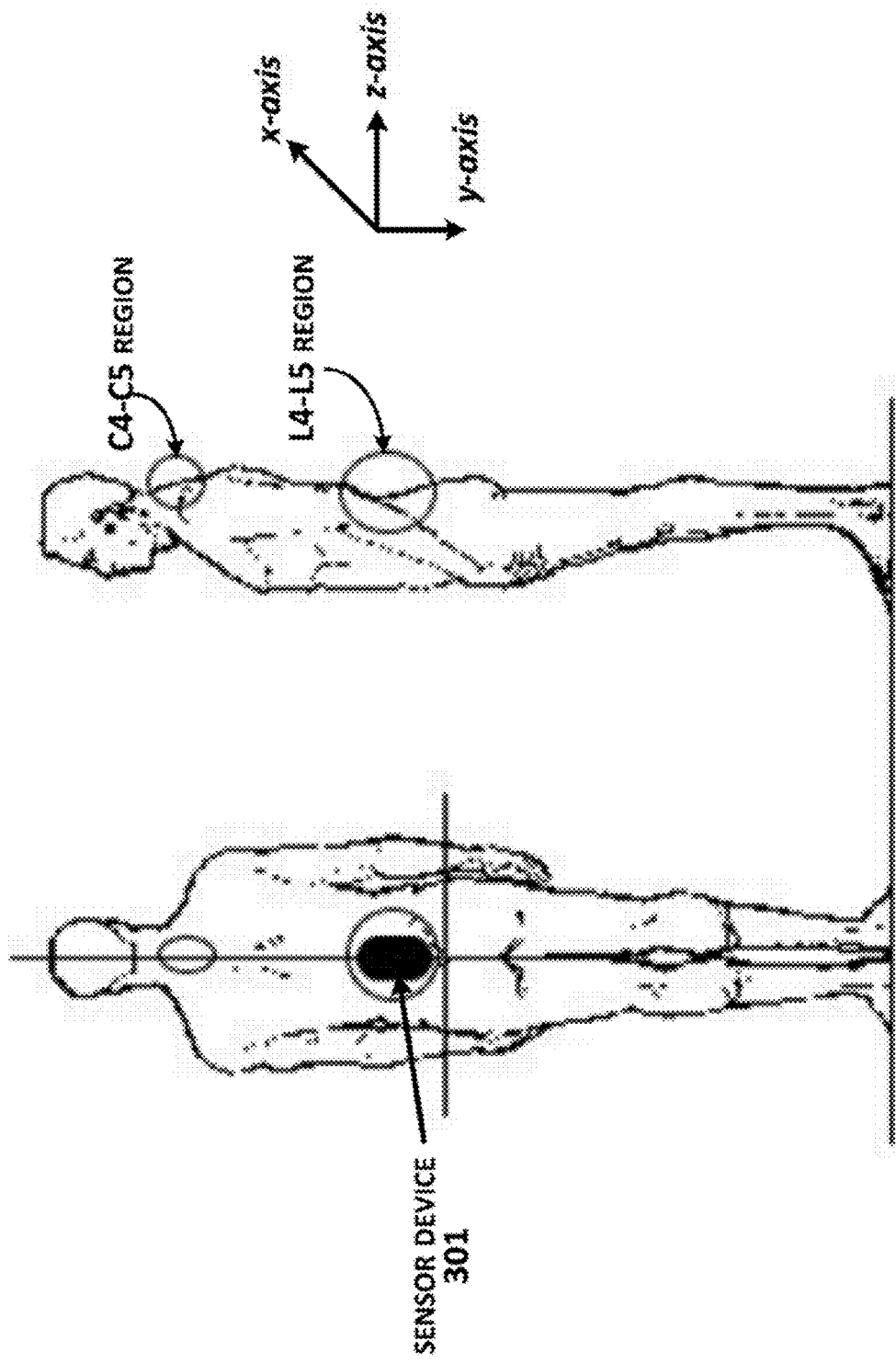
FIG. 5 is a diagram depicting appropriate placement of a sensor device according to one embodiment.

Referring now to FIG. 5, sensor device 301 can be attached to a body in various locations. For example, as indicated, sensor device 301 can be attached to a user's back (e.g., in a belt or band embodiment) at the level of the L4-L5 vertebrae (i.e., at the pelvis just below the waist) and/or attached to a user's back (e.g., in an adhesive patch embodiment) at the level of the S1-S2 vertebrae (i.e., at the pelvis a few inches below the waist), and/or attached to the user's neck at the level of the C4-C5 vertebrae (i.e., on the back of the neck a few inches from the base of the head). Once sensor device 301 is attached, many variables can affect data obtained from accelerometer 405. For example, differences in user body characteristics, belt models, shoes, manufacturing tolerances, etc. can cause variability in the accelerometer measurements by altering alignment of the accelerometer axes with the three-dimensional axes in reality (e.g., high heels may tilt a user's spine forward such that the y-axis of the user measured by accelerometer 405 is no longer a truly vertical y-axis in space). Additionally, the user might apply the sensor in an upside-down orientation. Or, orientation of accelerometer 405 on sensor circuit board 402 can change between product releases.

Effects of these and other factors can be minimized with a procedure to normalize accelerometer measurements so that the measurements from accelerometer 405 indicating acceleration along the x-, y-, and/or z-axes correspond to movement of body position along those axes. Accelerometer 405 can be imagined as having three perpendicular axes, with weights on springs sliding along the axes. The x and z weights are in the middle of their respective axes, representing an accelerometer reading of x=0 and z=0. Gravity pushes down the weight on the y-axis, resulting in a reading of 1 G for y.

To control for these effects, in one embodiment, accelerometer 405 is calibrated and normalized so as to align the x-, y-, and z-axes to a correct orientation wherein accelerometer data deviations from zero on the x-axis indicate a lateral (side-to-side) movement of the user, accelerometer data deviations from zero on the y-axis indicate a vertical (up and down) movement of the user, and accelerometer data deviations from zero on the z-axis indicate a transverse (rocking, e.g., dorsal-to-ventral) movement of the user.

If the accelerometer is normalized correctly, horizontal movement (e.g., leaning left or right) should result in non-zero x-values as the imagined x-weight slides away from the point where the axes meet and forwards or backwards movement (e.g., leaning forwards or backwards) should result in non-zero accelerometer z-values as the imagined z-weight slides away from the point where the axes meet. Since gravity normally slides the imagined weight along the y-axis, free-fall would result in y=0 (followed by a large value for y when the user hits the ground).

Sensor Orientation Normalization.

One embodiment of normalization will now be discussed in more detail. A known difficulty with using an accelerometer on a user is that the three axes are rotated in some unknown way because of the variables discussed above. Thus, a rotation matrix $R_0$ is used to align the accelerometer with gravity such that $$R_0 \begin{pmatrix} x_0 \\ y_0 \\ z_0 \end{pmatrix} = \begin{pmatrix} 0 \\ 1 \\ 0 \end{pmatrix}$$

where $(x_0, y_0, z_0)$ is a first accelerometer measurement when the user is standing with good posture.

Unfortunately, the single rotation matrix $R_0$ will not necessarily conform to the requirement that z should remain 0 if the user leans right, and that x should remain 0 if the user leans back. And even if these requirements are met, the signs of the measurements could still be inverted.

To deal with this issue, a second measurement $(x_1, y_1, z_1)$ is taken when the user is sitting in a chair and leaning back. After putting this measurement vector through the rotation $R_0$, a second rotation $R_1$ around the y-axis is used to align the accelerometer with a y-plane of the x, y, z coordinate system such that $$R_1 R_0 \begin{pmatrix} x_1 \\ y_1 \\ z_1 \end{pmatrix} = \begin{pmatrix} 0 \\ \tilde{y}_1 \\ \tilde{z}_1 \end{pmatrix}$$

where $\tilde{y}_1$ is the y-axis coordinate after two rotations and $\tilde{z}_1$ is the z-axis coordinate after two rotations. Because $R_1$ rotates around y, the axial matrix is still $$R_1 R_0 \begin{pmatrix} x_0 \\ y_0 \\ z_0 \end{pmatrix} = \begin{pmatrix} 0 \\ 1 \\ 0 \end{pmatrix}$$

The orientation matrices $R_0$ and $R_1$ are computed at least once for a user and can then be stored in memory and reused. If the user wears the sensor in a different way, or switches to a substantially different pair of shoes, a new set of matrices is needed, so the user recalibrates and renormalizes sensor device 301.

One challenge is how to get the user to stand with good posture in order to take baseline accelerometer measurements $(x_0, y_0, z_0)$. Explaining good posture to each user so s/he can provide appropriate input (i.e., move appropriately) to make sensor device 301 work in a meaningful way is impractical. Fortunately, an average measurement $(\bar{x}_w, \bar{y}_w, \bar{z}_w)$ of a walking user provides an excellent approximation of the needed good posture measurement $(x_0, y_0, z_0)$. Thus, the user is instructed to walk naturally for about twenty seconds while wearing sensor device 301, during which period microprocessor 403 records a number of measurements (e.g., 750 measurements) from accelerometer 405. The average of the sampled walking measurements is then used to compute $R_0$.

To increase the quality of the samples, microprocessor 403 applies a simple motion detection procedure (which works regardless of sensor orientation) to identify aberrant measurements that were obviously not produced by a walking user. In one embodiment, accelerometer data $(x_t, y_t, z_t)$ are collected for every time t (e.g., at 32 Hz). Power at each time point $(A_t)$ is computed using the equation $$A_t = \ln(x_t^2 + y_t^2 + z_t^2).$$

Power is compared over successive data points. A change in power $(D_t)$ over successive data points $(A_t$ and $A_{t-1})$ indicates movement. The time series $D_t$ is then smoothed using the equation $$S_t = 32 D_t + \sum_{k=1}^{31} (32-k)(D_{t+k} + D_{t-k})$$

where S is the smoothed time series, D is a change in power, t is a time index, and k is a looping index. $S_t$ is then compared to defined thresholds to determine whether the subject is walking or sitting at time t. For example, if the accelerometer is configured such that gravity is represented by a value of 248, the threshold to identify a walking state is, e.g., 160 and the threshold to identify a sitting state is, e.g., 45. Thus, if $S_t$ is calculated to be 170 (i.e., greater than the walking threshold), a walking state is detected, whereas if $S_t$ is calculated to be 40 (i.e., less than the sitting threshold), a sitting state is detected. If $S_t$ values range between movement state thresholds (e.g., between 45 and 160 in this example), the sample is discarded due to classification uncertainty. In this way, aberrant measurements can be rejected from the sampled measurements before the average is computed.

The second measurement $(x_1, y_1, z_1)$ is easier to acquire. The user is instructed to sit in a chair and lean back. Although the user might lean back more or less than desired for good posture (e.g., depending on the chair or on personal preference), any such deviation does not impact $R_1$ directly. Leaning further back in the chair helps to improve accuracy of rotation, but does not impact an angle of rotation per se.

Calculation of $R_0$ and $R_1$.

Known algorithms can be used to compute the rotation matrices. A preferred process is presented below.

The first goal is to find a matrix $R_0$ such that $$R_0 \begin{pmatrix} x_0 \\ y_0 \\ z_0 \end{pmatrix} = R_0 v_0 = \begin{pmatrix} 0 \\ 1 \\ 0 \end{pmatrix}$$

where $v_0$ is the vector derived by averaging the walking samples. An assumption is made that that $|v_0|=1$, which assumption is plausible because gravity is, by definition, 1 G and all walking movements compensate each other. Experimentation indicates that the assumption is valid.

In a first step, $v_0$ is rotated around the z-axis by a rotation $R_z$ until the x-coordinate disappears (i.e., x becomes 0). Then a second rotation $R_x$ around the x-axis eliminates the z coordinate (i.e., z becomes 0) until eventually $$R_0 = R_x R_z$$

where $$R_z = \begin{pmatrix} \cos\varphi & -\sin\varphi & 0 \\ \sin\varphi & \cos\varphi & 0 \\ 0 & 0 & 1 \end{pmatrix},$$

$$R_x = \begin{pmatrix} 1 & 0 & 0 \\ 0 & \cos\theta & -\sin\theta \\ 0 & \sin\theta & \cos\theta \end{pmatrix},$$

angle $\phi$ is defined as $$\varphi = \text{sgn}(x_0)\text{acos}\left(\frac{y_0}{\sqrt{x_0^2 + y_0^2}}\right),$$

and angle $\theta$ ais defined as $$\theta = -\text{sgn}(z_0)\text{acos}\left(\frac{\sqrt{x_0^2 + y_0^2}}{|v_0|}\right).$$

The next goal is to find a matrix $R_1$ representing a rotation around the y-axis such that $$R_1 R_0 \begin{pmatrix} x_1 \\ y_1 \\ z_1 \end{pmatrix} = \begin{pmatrix} 0 \\ \tilde{y}_1 \\ \tilde{z}_1 \end{pmatrix}$$

where $(x_1, y_1, z_1)$ is an accelerometer measurement while the user is sitting comfortably in a chair, and $R_0$ is the rotation matrix derived from averaged accelerometer measurements while the user is walking.

$R_1$ can be computed as $$R_1 = \begin{pmatrix} \cos\varphi & 0 & \sin\varphi \\ 0 & 1 & 0 \\ -\sin\varphi & 0 & \cos\varphi \end{pmatrix}$$

where the angle $\phi$ is defined as $$\text{asin}\left(\frac{x_0}{\sqrt{x_0^2 + z_0^2}}\right).$$

After the data are normalized, microprocessor 403 stores the normalized data for analysis to determine the user's movement state and/or posture quality.

Biomechanical Posture Detection and Feedback.

Figure 6:
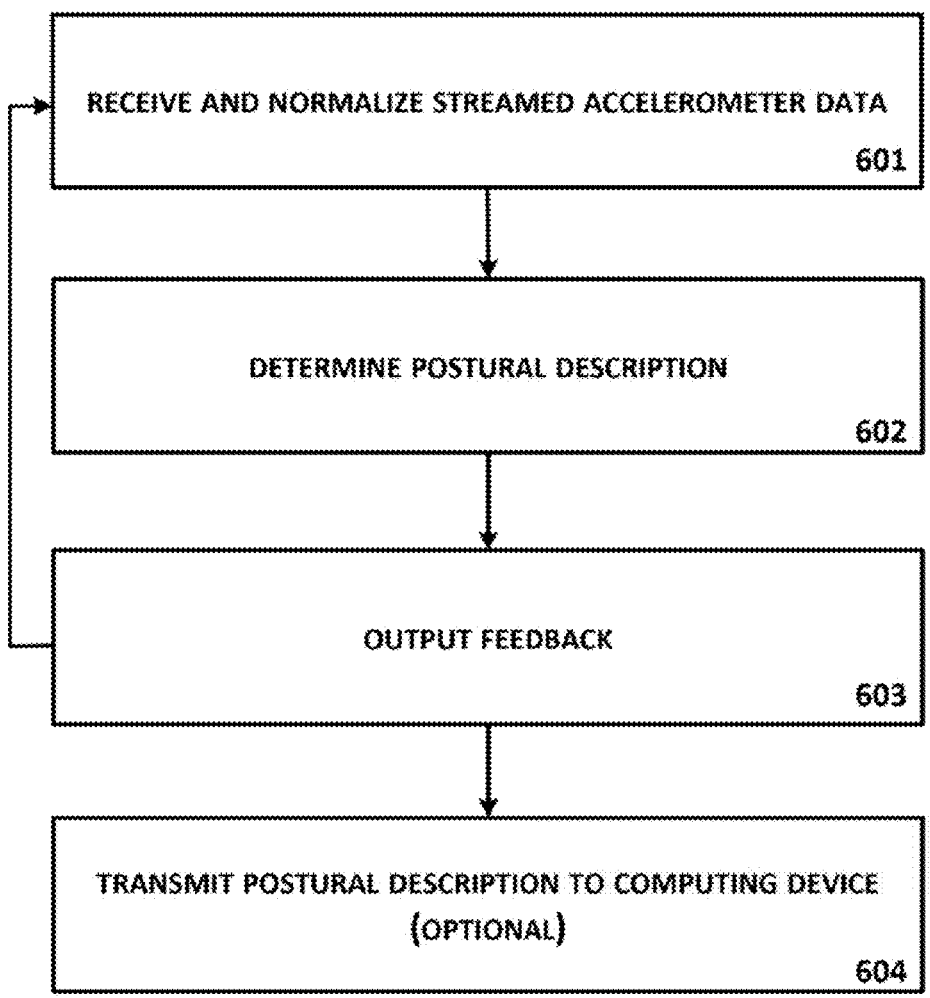
FIG. 6 is a flowchart detailing a method of biomechanical posture detection and feedback system according to one embodiment.

A flowchart of a method of biomechanical posture detection and feedback according to one embodiment is presented in FIG. 6. In step 601, microprocessor 403 receives and normalizes accelerometer data streamed from accelerometer 405 in real-time as discussed above. Once sensor device 301 has been normalized, sensor device 301 is used to detect posture of a user and provide sensory feedback to that user.

Figure 9:
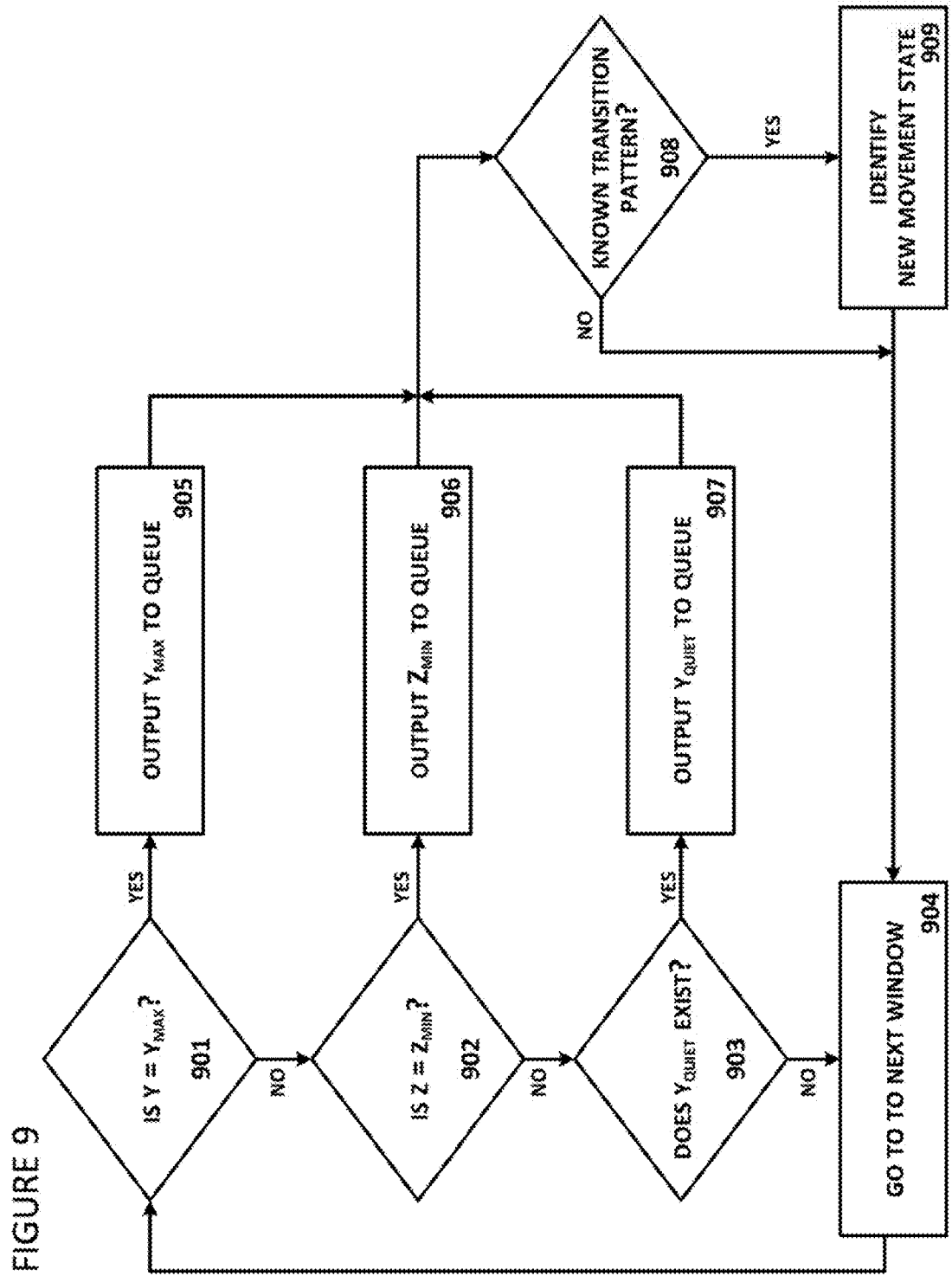
FIG. 9 is a flowchart detailing steps of a rule-based model to determine movement state according to one embodiment.

In step 602, microprocessor 403 analyzes the accelerometer data to determine the real-time movement state and/or postural state of the user. The user's movement state (e.g., standing, sitting, lying, running, or walking, discussed further herein with respect to FIGS. 9 and 10) and posture quality (i.e., how well the user is balanced within that movement state, e.g., whether and how well the user's posture matches a desirable "good posture" for the determined movement state) together form a postural description of the user. In various embodiments, the user's movement state is determined by a library comparison model, a rule-based model, a statistical model, and/or a tilt angle model, each of which are described elsewhere herein. The tilt angle model is also used to determine a user's posture quality. The real-time postural description information is time-stamped and stored in memory, and can be retrieved from memory for future analysis (e.g., comparison to incoming accelerometer data) and/or for later synchronization with computing device 303 and/or cloud server 305.

In step 603, microprocessor 403 triggers actuator 406 to output sensory feedback to the user based on the determined real-time postural description of the user. Steps 601, 602, and 603 are looped continuously in real-time as long as the user has an attached operating sensor device 301.

In optional step 604, microprocessor 403 transmits the time-stamped postural descriptions to computing device 303 on which an application is running to display feedback on a display screen of computing device 303. Step 604 can be looped continuously with steps 601, 602, and 603 in real-time. Alternatively, step 604 can occur when the application on computing device 303 is accessed, at which point sensor device 301 synchronizes data with computing device 303.

Movement State Determination

As discussed with reference to step 602, microprocessor 403 determines the movement state of a user. To do this, microprocessor 403 analyzes tri-axial acceleration data received from accelerometer 405 to determine user movements along the x-, y-, and z-axes indicative of movement states and/or transitions between the movement states. These accelerometer data can be categorized by microprocessor 403 using a state machine with multiple movement states (e.g., running, walking, standing, sitting, jumping, squatting, and lying), as depicted in the state diagram of FIG. 7.

Figure 10:
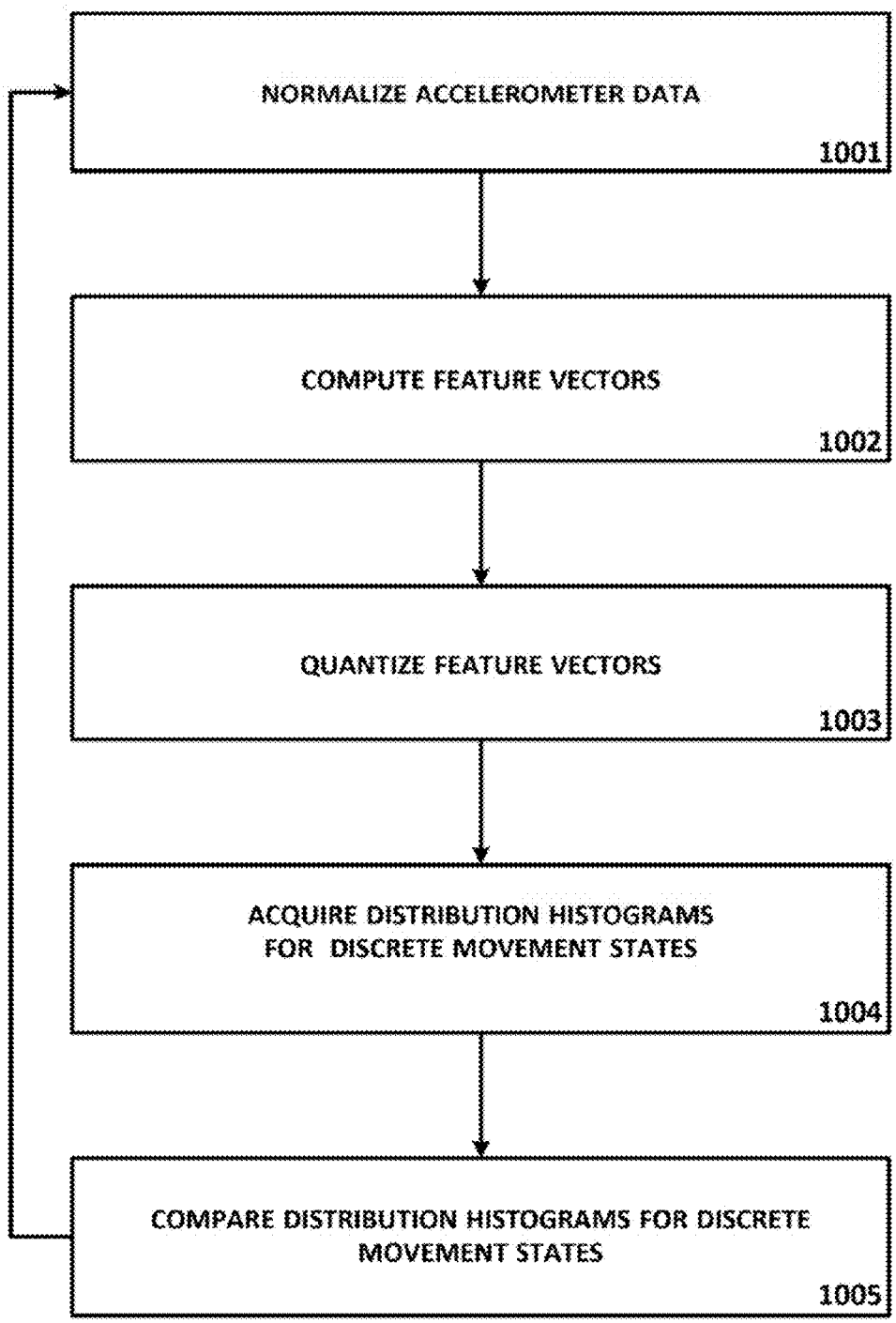
FIG. 10 is a flowchart detailing steps of a statistical model to determine movement state according to one embodiment.

Microprocessor 403 can determine the movement state of a user directly using a statistical model 702 (as detailed further herein with reference to FIG. 10). In some instances (e.g., when a user is lying), microprocessor 403 can use a pelvic tilt angle model 704 (as detailed further herein) to directly determine a user's movement state. Pelvic tilt angle model 704 is shown in the figure at only one state transition (between lying and running). One of skill in the art will understand, however, that this model can be used to determine transitions between lying and other movement states, as well as to directly determine a lying state.

Microprocessor 403 can also determine the user's movement state indirectly (using a library comparison model or a rule-based model) by analyzing accelerometer data to identify a state transition (indicated by linear arrows in the figure) indicative of a known transition between two known movement states. As an example, if microprocessor 403 identifies a state transition as a sitting-to-standing transition, microprocessor 403 determines that the user is moving into a standing state. If instead microprocessor 403 identifies a state transition as a sitting-to-lying transition, microprocessor 403 determines that the user is moving into a lying state. Microprocessor 403 assumes that the user remains in the determined movement state until a new state transition or state is detected. To identify state transitions, microprocessor 403 analyzes the accelerometer data using a library comparison model 703 (as detailed further herein), a rule-based model 701 (as detailed further herein with reference to FIG. 9), and/or a pelvic tilt angle model 704. Although library comparison model 703 and rule-based model 701 are depicted in the figure at only one state transition (e.g., between sitting and lying and between standing and sitting, respectively) one of skill in the art will understand that these models can be used for transitions between any two movement states.

Figure 8:
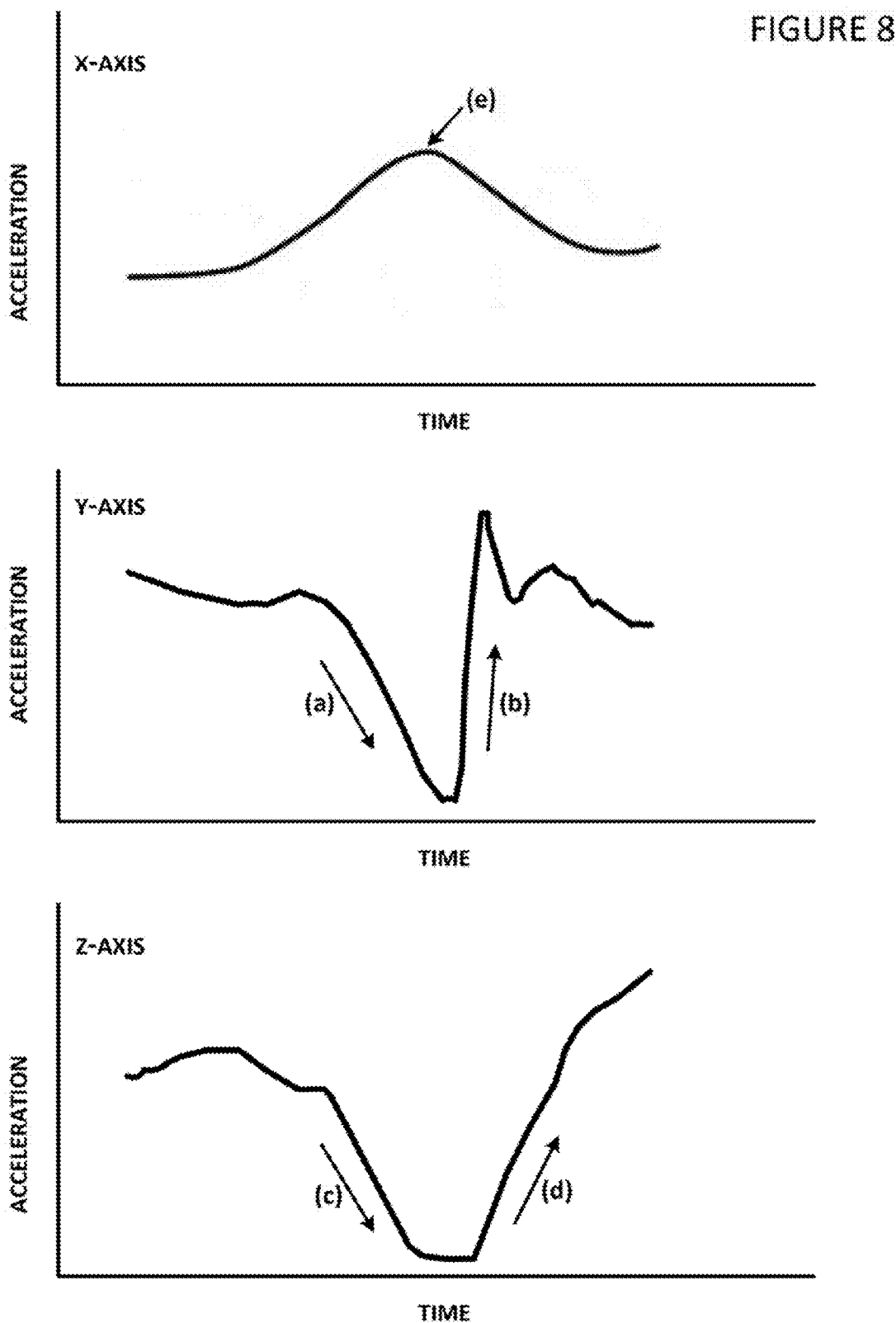
FIG. 8 illustrates an exemplar acceleration pattern of a user transitioning from a standing state to a sitting state.

State transitions have unique acceleration patterns. As shown in a graph of exemplar data in FIG. 8, as a user transitions from a standing to a sitting position, there is an initial moderate acceleration downward (a) along the y-axis as well as (c) along the z-axis, followed by (b) an immediate acceleration upward in the y-axis as the user hits the chair, and (d) a gradual increase in acceleration values as the user leans back into the chair. Moderate acceleration is seen along the x-axis and peaks (e) when the user hits the chair.

Although some aspects of the state transitions may be individual—and/or situation-specific (e.g., speed of the transition), tri-axial acceleration patterns of state transitions are similar across different individuals. Additionally, the tri-axial acceleration pattern for a transition from a first movement state (e.g., standing) to a second movement state B (e.g., sitting) is distinguishable from the acceleration pattern for a reverse transition from the second movement state (e.g., sitting) to the first movement state (e.g., standing) even though the tri-axial acceleration patterns for each state transition (e.g., standing to sitting transition) are similar across individuals. Thus, these tri-axial acceleration patterns can be used by microprocessor 403 to detect state transitions and thereby identify the movement states contributing to the state transition (i.e., a previous movement state and a current movement state). Once the current movement state is identified, a user is considered to remain within that movement state until a new state or state transition is detected.

Library Comparison Model.

With the library comparison model, state transitions are identified by comparing continuous real-time acceleration signals from accelerometer 405 with a movement library comprised of known state transition patterns. Known transition patterns are accelerometer signals accrued over time from multiple users for known transitions between two discrete states (e.g., accelerometer signals indicative of a transition between standing and sitting, between standing and walking, between walking and running, etc.). If a match is found between the real-time signal and a known transition pattern in the movement library, then the state transition is identified and stored in memory.

In one embodiment, real-time accelerometer data are stretched or compressed in time before comparison to the movement library in order to mimic a state transition being made more rapidly or less rapidly. As an example, a user slowly standing from a sitting position over, e.g., a 1-second time period, generates continuous real-time accelerometer data to be compared to transition patterns in the movement library. The 1-second period data are also compressed (e.g., to occur over a 0.5-second time period) and stretched (e.g., to occur over a 2-second time period). Thus, multiple data samples (e.g., 3 in this example) are compared to the movement library in order to find a match to a known state transition. Stated differently, if the real-time motion data are faster but qualitatively equivalent to a transition pattern in the movement library, stretching the real-time signal over a longer time period will yield a match with the transition signal in the movement library, thus allowing the state transition to be identified.

The library of patterns is built from historical measurements of users (with sensor device 301 attached) transitioning between movement states (e.g. standing up, sitting down, etc.).

Transitions involving a lying state, however, are determined by computing a pelvic tilt angle orientation (discussed elsewhere herein). For these transitions, if microprocessor 403 detects that the pelvic tilt angle orientation of accelerometer 405 meets a threshold indicating, e.g., an orientation less than 30 degrees with respect to the ground, then microprocessor 403 determines that the user is lying down. If a lying state is determined, the directionality (i.e., a user lying on his stomach vs. lying on his back) is determined by the orientation of the z-axis.

Microprocessor 403 stores a current state (i.e., the state at which the determined transition was completed, e.g., sitting if the determined transition was from standing to sitting) in memory with a time stamp. The current state is assumed to persist until microprocessor 403 receives real-time data from accelerometer 405 that is determined by microprocessor 403 to indicate another state transition (e.g., from sitting to lying). The time-stamped current state and time-stamped state transitions are stored in memory, and can be transferred at some time to computing device 303 when sensor device 301 is synchronized with computing device 303.

Rule-Based Model.

State transitions can also be determined by using a rule-based model. The rule-based model uses gliding sample windows to detect extrema of various different time-domain features (e.g., x, y, or z) and then analyzes the sequence of x, y, and z extrema and their properties (e.g., acceleration amplitude) with heuristic rules to look for state transitions. In one embodiment, microprocessor 403 analyzes data streamed in real-time (e.g., at 32 Hz) from accelerometer 405 using a sliding sample window (e.g., a 32-sample window such that a first window contains accelerometer data points in 1-32, a second window contains data points in frames 2-33, a third window contains data points in frames 3-34, etc.). Thus, data for a certain percentage of a movement or movement transition is captured within each window. Microprocessor 403 analyzes the streamed accelerometer data in sample windows to identify a maximum y-value ("$y_{max}$", indicative of maximal vertical acceleration), a minimum z-value ("$z_{min}$", indicative of minimal forwards/backwards acceleration), and a quiescence signal value ("$y_{quiet}$", indicative of minimal acceleration in the y-axis). As these values are identified, they are fed into a 3-element queue. When the queue contains 3 values that match a pattern associated with a known transition (i.e., between known movement states), microprocessor 403 can identify the movement state. A flowchart detailing steps of a method to determine movement state using this digital signal processing model according to one embodiment is presented in FIG. 9.

In step 901, microprocessor 403 determines whether $y_t = y_{max}$. Microprocessor 403 makes this determination by comparing the current y-value $y_t$ to all y-values of an immediately preceding window $w_p$ and to all y-values of an immediately succeeding window $w_s$. Mathematically, if $y_p < y_t$ for all $y_p$ in $w_p$ and if $y_t > y_s$ for all $y_s$ in $w_s$, then $y_t = y_{max}$ If $y = y_{max}$, then, in step 905, an indicator of $y_{max}$ (e.g., a nominal tag, e.g., "A" or "max"), an accelerometer measurement associated with that $y_{max}$, and a time stamp associated with that accelerometer measurement, are output as one value (with features of indicator, gravity, time) to the 3-element queue.

If $y \ne y_{max}$, then, in step 902, microprocessor 403 determines whether $z_t = z_{min}$. Microprocessor 403 makes this determination by comparing the z-value of the current z-value $z_t$ to all z-values of the immediately preceding window $w_p$ and to all z-values of the immediately succeeding window $w_s$. Mathematically, if $z_p > z_t$ and if $z_t < z_s$, then $z_t = z_{min}$.

If $z = z_{min}$, then, in step 906, an indicator of $z_{min}$ (e.g., a nominal tag, e.g., "B" or "min"), an accelerometer measurement associated with that $z_{min}$, and a time stamp associated with that accelerometer measurement, are output as one value (with features of indicator, gravity, time) to the 3-element queue.

If $z \neq z_{min}$, then, in step 903, microprocessor 403 determines whether $y_{quiet}$ exists. Microprocessor 403 makes this determination by comparing local y-values (i.e., values of y within the current window). One of skill in the art will understand that the sample window used to determine $y_{quiet}$ need not contain the same number of samples as the sample window used to calculate $y_{max}$ and $z_{min}$. If the maximum y-value within the current window is close to the minimum y-value within the current window (e.g., +/−5 where 250 is 1 G, which is to say, a y range is 0.02 G's), then the midpoint between the maximum and minimum y-values is determined to be $y_{quiet}$.

If $y_{quiet}$ exists within a current window, then, in step 907, an indicator of $y_{quiet}$ (e.g., a nominal tag, e.g., "C" or "quiet"), an accelerometer measurement associated with that $y_{quiet}$, and a time stamp associated with that accelerometer measurement, are output as one value (with features of indicator, gravity, time) to the 3-element queue.

If $y_{quiet}$ does not exist within the current window, then, in step 904, microprocessor 403 loops back to step 901, a next window becomes a new current window, and microprocessor 403 begins analyzing y-/z-values in the new current window.

In step 908, microprocessor 403 determines whether the pattern of values in the queue (the "queue pattern") matches a pattern associated with a known transition between movement states. For example, if the queue pattern is ordered as "min-max-quiet" (or "B-A-C"), the queue matches a known pattern for a transition from a standing to a sitting state. Or, if the queue pattern is ordered as "quiet-max-min" (or "C-A-B"), the queue matches a known pattern for a transition from a sitting to a standing state.

If, in step 908, microprocessor 403 determines that the queue pattern is a known state transition pattern, then, in step 909, microprocessor 403 identifies a new movement state associated with that state transition pattern and stores that information with a time-stamp in memory.

If microprocessor 403 determines that the queue pattern is not a known state transition pattern (in step 909), then, in step 904, microprocessor 403 loops back to step 901, a next window becomes a new current window, and microprocessor 403 begins analyzing y-/z-values in the new current window.

One of skill in the art will recognize that steps 901, 902, and 903 need not be performed in the order described herein, but may be performed simultaneously, in reverse order, or otherwise. One of skill in the art will further understand that as new values are placed into the queue, older values are displaced (pushed out) from the queue. Thus, the pattern within the queue changes each time a newly identified $y_{max}$, $z_{min}$, or $y_{quiet}$ is identified by microprocessor 403.

Tilt Angle Model.

Tri-axial acceleration patterns can distinguish transitions involving most states, but are less robust for determining transitions to and/or from a lying state. These transitions (involving a lying and/or sitting state) can be better distinguished using a pelvic tilt angle model. If microprocessor 403 detects that the pelvic tilt angle (as measured by orientation of accelerometer 405) meets a threshold indicating, e.g., an orientation of less than 30 degrees, microprocessor 403 determines that the user is lying down. If a lying state is determined, the directionality (i.e., a user lying on his stomach vs. lying on his back) is determined by the orientation of the z and x axes.

Statistical Model.

Figure 7:
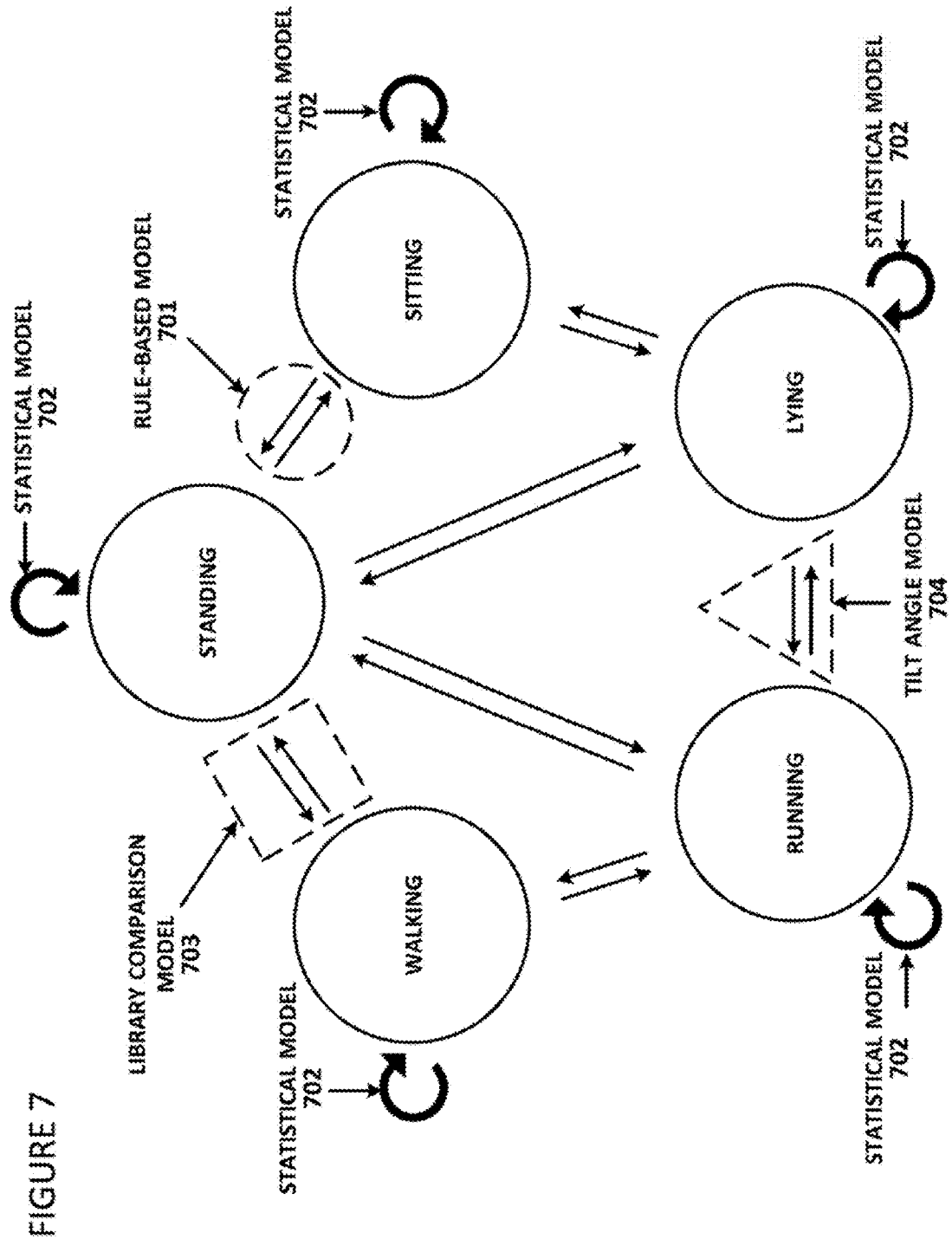
FIG. 7 is a state diagram illustrating various movement states and transitions between those movement states according to one embodiment.

As discussed with reference to FIG. 7, microprocessor 403 can determine the movement state of a user directly using a statistical model 702. Because microprocessor 403 runs the statistical model continuously on incoming data from accelerometer 405 (as indicated by circular arrows next to each state in the figure), microprocessor 403 can determine when the user moves from one state (e.g., sitting) into a different state (e.g., standing). A flowchart of a method to determine movement state through a statistical model according to one embodiment is presented in FIG. 10, although the details of each step are discussed in further detail with respect to exemplar data.

In step 1001, microprocessor 403 normalizes accelerometer data.

In step 1002, microprocessor 403 computes feature vectors to reduce dimensionality of the accelerometer data.

In step 1003, microprocessor 403 quantizes the feature vectors and uses clustering techniques to assign the quantized feature vectors to Gaussian distributions.

In step 1004, microprocessor 403 acquires estimated probability histograms for discrete movement states.

In step 1005, microprocessor 403 determines the movement state by comparing probabilities of different movement states.

These steps of the statistical model will now be explained in greater detail by way of example.

In real-time, microprocessor 403 retrieves accelerometer measurements at 32 Hz (i.e., 32 three-dimensional vectors (x, y, z) per second). In the following example, three exemplar vectors (e.g., measured vectors v1, v2, and v3 of 32 vectors over frames 1, 2, and 3 respectively of a one second, 32-frame period) are used, representing about a tenth of a second of data recorded from a walking person.

Accelerometer 405 is a 10-bit accelerometer with output values ranging from −512 to 511. Gravity corresponds to a reading of 248. Thus, if the user remains stationary, with 0 movement in two axes, the third axis shows a reading of 248. The exemplar measured vectors v1, v2, and v3 are, respectively, $$\begin{pmatrix} 271 \\ 32 \\ -148 \end{pmatrix}, \begin{pmatrix} 310 \\ -87 \\ -100 \end{pmatrix}, \begin{pmatrix} 287 \\ -76 \\ 20 \end{pmatrix}$$
$$\quad v1 \qquad\quad v2 \qquad\quad v3$$

Normalization of Accelerometer Data (Step 1001).

In step 1001, incoming vectors 1, 2, and 3 are rotated to normalize the accelerometer orientation. Two rotations ($R_0$ and $R_1$) are performed concurrently to find orientation matrices $R_0$ (representing a rotation around the z-axis) and $R_1$ (representing a rotation around the y-axis) such that $$\begin{pmatrix} \tilde{x} \\ \tilde{y} \\ \tilde{z} \end{pmatrix} = R_1 R_0 \begin{pmatrix} x \\ y \\ z \end{pmatrix}$$

These orientation matrices ($R_0$ and $R_1$) are computed at least once for a user and then stored in memory so they need not be recomputed each time measurements are received from accelerometer 405.

Using the exemplar vectors, $$R_0 = \begin{pmatrix} -0.0166 & -0.9999 & 0 \\ 0.9703 & -0.0161 & -0.2414 \\ 0.2414 & -0.0040 & 0.9704 \end{pmatrix}$$

and $$R_1 = \begin{pmatrix} -0.9974 & 0 & 0.0724 \\ 0 & 1 & 0 \\ 0.0724 & 0 & -0.9974 \end{pmatrix}$$

Sending the three exemplar vectors through this transform results in rotated vectors $$\begin{pmatrix} 30.74 \\ 298.16 \\ 80.78 \end{pmatrix}, \begin{pmatrix} 83.20 \\ 326.33 \\ 15.89 \end{pmatrix}, \begin{pmatrix} 64.59 \\ 274.87 \\ 93.90 \end{pmatrix}$$
$$v1 \quad\quad v2 \quad\quad v3$$

Computation of Feature Vectors (Step 1002).

Even after normalizing accelerometer orientation, the raw three-dimensional vectors can be improved for activity recognition. Thus, in step 1002, microprocessor 403 computes feature vectors from the raw three-dimensional normalized vectors. Because microprocessor 403 has limited memory (e.g., 8 KB of RAM) and limited computing power (e.g., 16 bit, 20 MHz) in one embodiment, a set of two features ($\alpha$, $\beta$) are calculated for use in lieu of these typical transformations:

$$\alpha_t = sgn(z) * \sqrt{x^2 + z^2}$$

and $$\beta_t = \alpha_t - \alpha_{t-1}$$

where t is a time index.

Using this feature set ($\alpha$, $\beta$) reduces dimensionality while adding motion-related information because $\beta$ measures the difference between the current and previous value of $\alpha$.

The three example vectors are now reduced to:

$$\begin{pmatrix} 86.43 \\ 0 \end{pmatrix}, \begin{pmatrix} 84.70 \\ -1.73 \end{pmatrix}, \begin{pmatrix} -113.97 \\ -198.68 \end{pmatrix}$$
$$v1 \quad\quad v2 \quad\quad v3$$

Note that $\beta_0=0$ by default because no previous value exists (before v1 at the first time point) from which to compute a difference.

Quantization of Feature Vectors (Step 1003).

After the feature vectors are computed, then in step 1003, the feature vectors are put through a process called vector quantization in which the vectors are restricted to discrete values (rather than a continuous set of values such as raw accelerometer data).

Incoming, rotated measurement vectors are assigned to an inventory of Gaussian distributions (a multivariate Gaussian mixture model) that the vector best matches. Density values of the vectors are used as a metric to identify the best matching distribution. Once a distribution is identified that best matches the incoming rotated measurement vector, the original vector is ignored, and microprocessor 403 instead uses an index of the best-matched distribution for remaining calculations.

In other words, the sequence of (exemplar) vectors is mapped to a sequence of integers:

$$v_1, \ldots, v_n \mapsto c_1, \ldots, c_n$$

where each $c_i$ is an integer representing the Gaussian distribution $g_{c_i}$.

In one embodiment, the multivariate Gaussian mixture model is derived with a clustering procedure (e.g., using an mclust package of an R platform analytics program (TIBCO Software Inc., Palo Alto, Calif.)). Input for the clustering procedure is a large collection of feature vectors $$\begin{pmatrix} \alpha \\ \beta \end{pmatrix}$$

in a comma-delimited file. The R commands to read the file and perform the clustering are:

```
> data <- read.csv(file="myfile.csv",head=TRUE,sep=",")
> mycols <- data[,c('XZ_ROT','DELTA_XZ_ROT')]
> mc<-Mclust(mycols,G=1:100,modelNames="EVI")
> sink("c:/mydir/mymixture.txt", append=FALSE, split=FALSE)
> mc$parameters
> sink()
```

The output of this procedure is a set of, at most, 100 normal distributions, each with an a priori probability. The overall density value of a vector v is given by $$f(v) = \Sigma \pi_c f(v, \mu_c, \Sigma_c)$$

where c is an index of looping through all the clusters, $\pi_c$ is an a priori probability of a cluster c, $\mu_c$ defines a cluster center, and $\Sigma_c$ is a covariance matrix. The term $f(v, \mu_c, \Sigma_c)$ denotes a multivariate Gaussian with parameters $\mu_c$ and $\Sigma_c$. The R platform program assumes an equal volume independent ("EVI") model, which means that covariance matrices $\Sigma_c$ are diagonal and of equal volume. In a two-dimensional case with k as a cluster index, $$\Sigma_k = (\sigma_k(\alpha), \sigma_k(\beta)).$$

The equal volume assumption means that $$\sigma_k(\alpha)\sigma_k(\beta) = \sigma_i(\alpha)\sigma_i(\beta) \text{ for all } i,k.$$

(As is known, this expression is called volume in analogy to the area (or volume) of an ellipse whose major and minor axis are $\sigma_k(\alpha)$ and $\sigma_k(\beta)$.)

Exemplar vector v (e.g., $v_1$, $v_2$, or $v_3$) is assigned to cluster c if $$\pi_c f(v, \mu_c, \Sigma_c) \geq \pi_d f(v, \mu_d, \Sigma_d) \text{ for all clusters } d.$$

Due to the EVI assumption, it is not necessary to compute a value of normal distributions for all d (e.g., v, $\mu_d$, $\Sigma_d$). Instead, a Mahalanobis distance can be used to arrive at the exact same result:

$$2\ln\pi_c + \frac{(\alpha - \mu_c(\alpha))^2}{\sigma_c^2(\alpha)} + \frac{(\beta - \mu_c(\beta))^2}{\sigma_c^2(\beta)} \leq 2\ln\pi_d + \frac{(\alpha - \mu_d(\alpha))^2}{\sigma_d^2(\alpha)} + \frac{(\beta - \mu_d(\beta))^2}{\sigma_d^2(\beta)}$$

for all clusters d.

Figure 11:
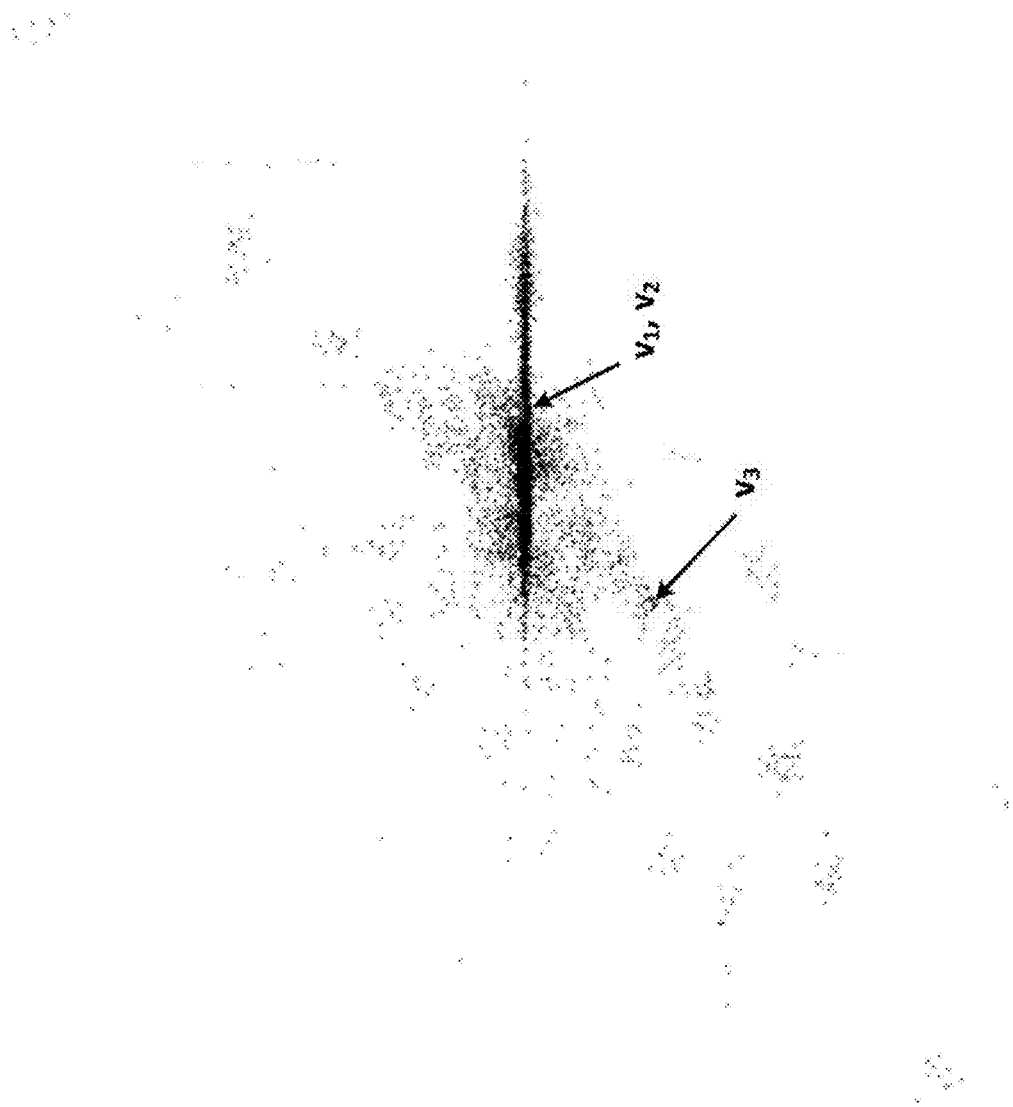
FIG. 11 is an exemplar mixture model for exemplar data clusters according to one embodiment.

The clusters can be visualized graphically by writing a program that generates samples from the Gaussian distributions with the help of a random number generator. When this is done, the mixture model consists of each Gaussian distribution represented by a cloud with an a priori probability. The mixture model for the exemplar data clusters are shown in FIG. 11. Arrows in the figure represent a location of the first two exemplar vectors ($v_1$, $v_2$) which are so closely located as to be indistinguishable in the figure and the third exemplar vector ($v_3$). Thus, vector quantization reduces exemplar input measurements to a sequence 43, 43, 17—that is, to the integer representing the distribution most closely matched by each exemplar vector.

Estimation of Distribution Histograms for Discrete Movement States (Step 1004).

In step 1004, microprocessor 403 acquires estimated distribution histograms for discrete movement states. In one embodiment, microprocessor 403 estimates the distribution histograms, while in other embodiments microprocessor 403 retrieves the distribution histograms from computing device 303 or via computing device 303 from cloud server 305. Regardless, the distribution histograms are estimated as follows. Given an integer sequence $c_1, \ldots, c_n$ (representing Gaussian distributions 1 through n) of quantized accelerometer readings (i.e., representing $v_1, \ldots, v_n$), and knowing that the sequence was generated while performing a known state (e.g. walking), a frequency of each cluster for that activity can be estimated to generate a discrete probability histogram of the clusters for each activity. These histograms are evaluated to determine the user's movement state. In each histogram, the probability of the clusters for that activity sum to 1.

For the determined integer sequence of the quantized vectors (e.g., the exemplar sequence 43, 43, 17), probabilities are determined from cluster histograms for the movement states. An estimated exemplar cluster histogram for a walking state is presented in FIG. 12 and for a running state in FIG. 13. Probabilities from these histograms are used to determine a probability for each integer of the exemplar sequence.

Figure 12:
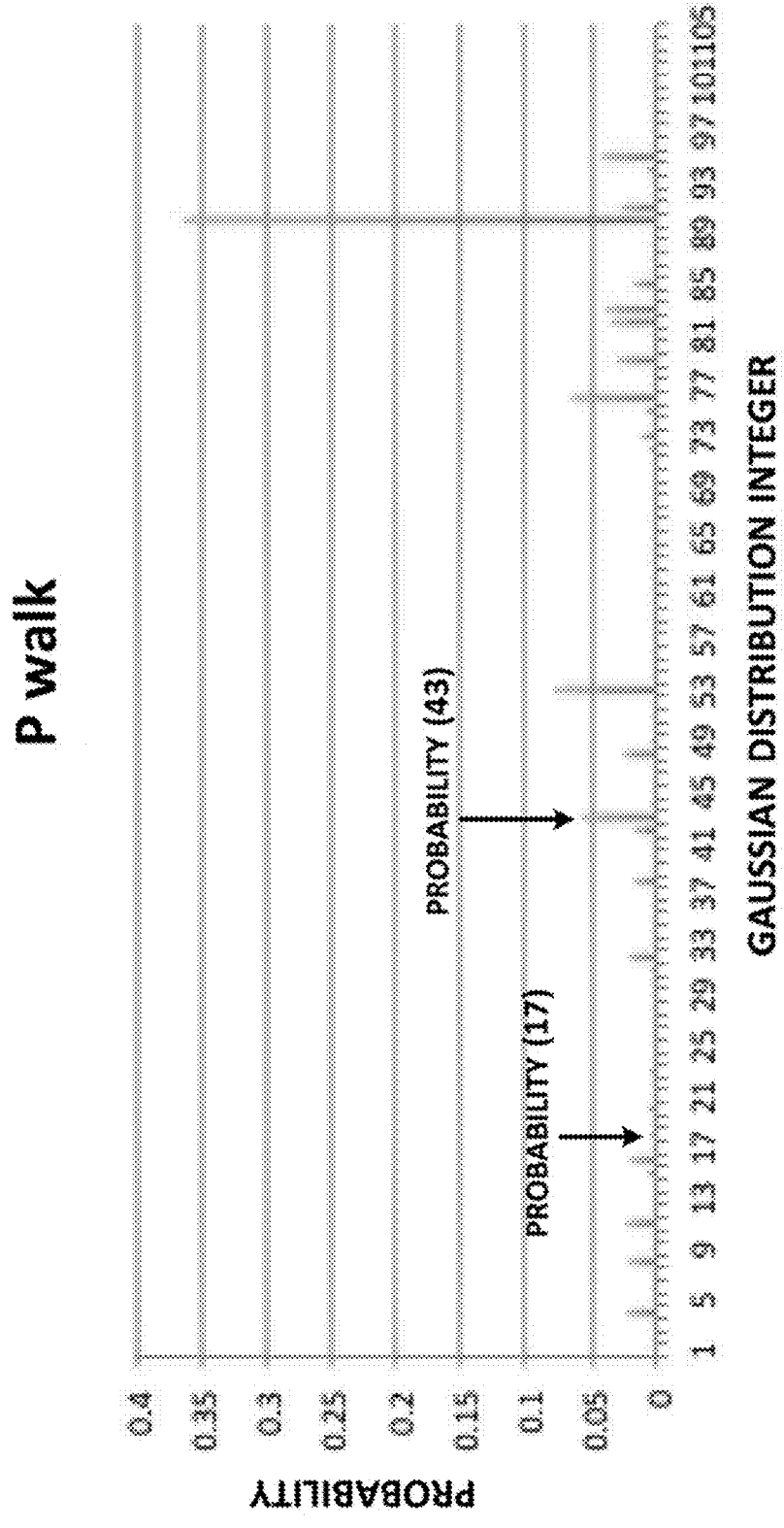
FIG. 12 is an illustration of exemplar estimated cluster distribution histograms for a walking state according to one embodiment.
Figure 13:
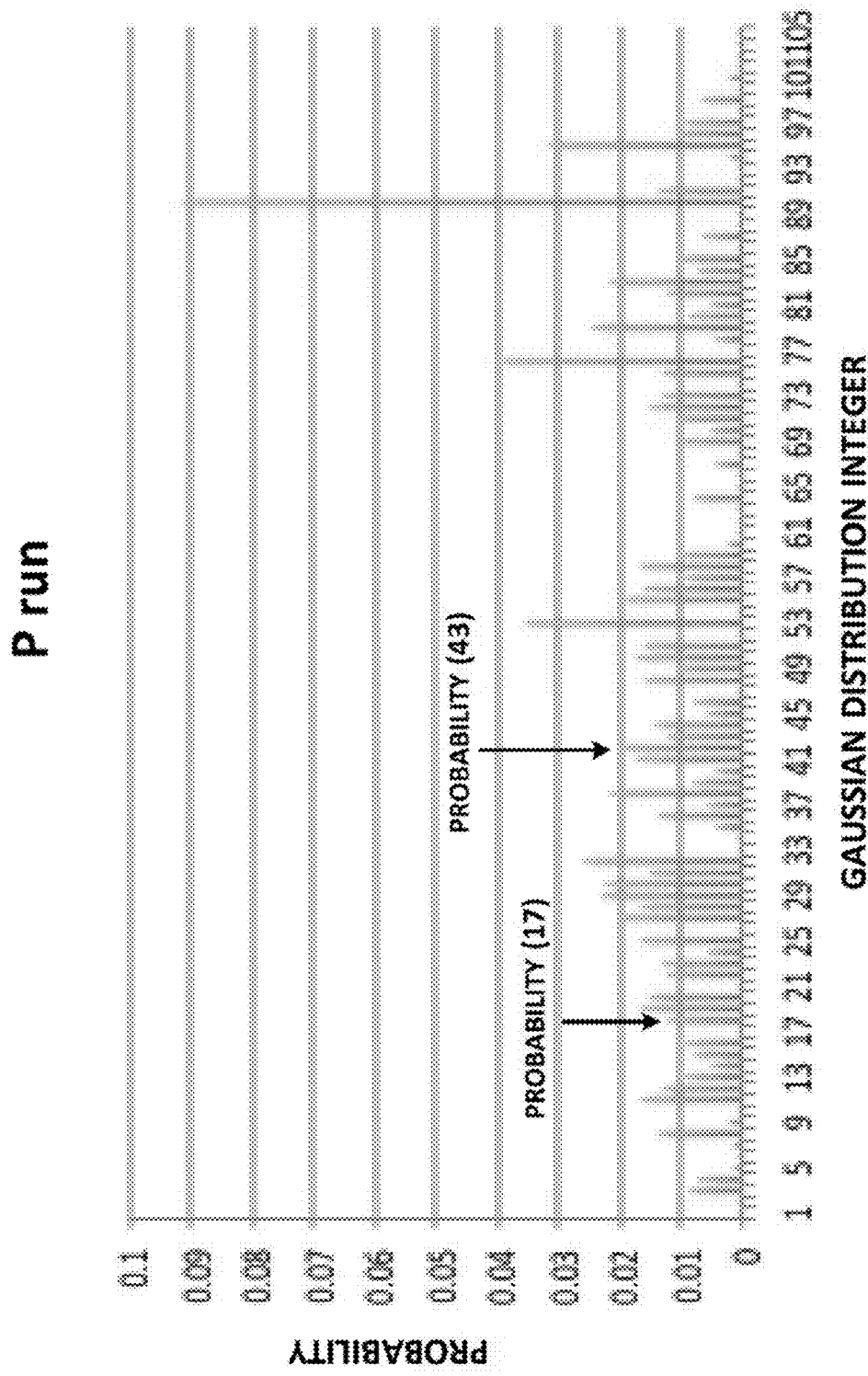
FIG. 13 is an illustration of exemplar estimated cluster distribution histograms for a running state according to one embodiment.

To determine a probability that a user is in a particular movement state, microprocessor 403 multiplies the probabilities (from the cluster histogram for the particular state) of the sequence integers (43, 43, 17). In FIGS. 12 and 13, the probabilities for the sequence integers are circles indicated with arrows. Thus, the probability that the user is in a walking state is:

$$P(\text{walk}) = P_w(43) P_w(43) P_w(17) = 0.0168 * 0.0168 * 0.0043 = 1.214 \times 10^{-6}$$

Likewise, the probability that the user is in a running state is:

$$P(\text{run}) = P_r(43) P_r(43) P_r(17) = 0.0216 * 0.0216 * 0.0129 = 6.02 \times 10^{-6}$$

Comparison of Distribution Histograms for Discrete Movement States (Step 1005).

In step 1005, microprocessor 403 determines a user's current movement state by comparing the separate probabilities for the integer sequence in discrete movement states to determine which movement state is most likely. In the exemplar data, the probability that the user is in a running state ($6.02 \times 10^{-6}$) is greater than the probability that the user is in a walking states ($1.214 \times 10^{-6}$). Thus, running is the determined state indicated by the exemplar data.

After evaluating the determined statistical model, microprocessor 403 stores the determined state in memory and loops back to step 1001 to begin the process again by normalizing a next set of accelerometer data vectors. By continually performing this process, microprocessor 403 can identify when the user has moved into a new movement state.

For longer sequences, however, three issues arise:

How to prevent numeric underflow which can occur because multiplying probabilities results in ever smaller numbers;

How to adapt probabilities over time since a new state (e.g., walking) must be detectable even after a user has been in a different state (e.g., running) for a long period of time; and How to adjust for clusters with a probability of 0 for an activity since such clusters necessarily drive an overall multiplicative probability for the activity to zero (from which no recovery is possible).

Underflow Issue.

In one embodiment, to prevent the numeric underflow problem, natural logarithms of the probabilities are used instead of the probabilities themselves. Conveniently, this adjustment also converts multiplicative probability calculations into additive calculations to generate log probability scores (and also saves some processing time). For the exemplar data, then, $$\ln P(\text{walk}) = \ln P_w(43) + \ln P_w(43) + P_w(17) = -5.54 - 5.54 - 5.45 = -16.53$$

$$\ln P(\text{run}) = \ln P_r(43) + \ln P_r(43) + P_r(17) = -3.84 - 3.84 - 5.45 = -13.13$$

As with linear probabilities as discussed elsewhere herein, microprocessor 403 compares the log probabilities to determine that, since the log probability of running ($-13.13$) is greater than that of walking ($-16.53$), running is the more likely movement state. As P approaches 0, log probability scores (i.e., $\ln(P)$) approach negative infinity, but very slowly, so the calculated log probabilities are not as small as those calculated as linear probabilities.

Adaptation Over Time Issue.

Probabilities for different activity states should not drift apart too much otherwise an hour of one state (e.g., walking) would be necessary to compensate for an hour of a different state (e.g., running). To avoid this problem, in one embodiment, the log of the determined activity (e.g., running in the exemplar data) is scaled to some fixed target log probability $\ln(P_T)$, and all other log probabilities are multiplied by that scaling adjustment factor. This scaling adjustment occurs during every data processing frame (i.e. 32 times a second). The target log probability also provides a mechanism to adjust the responsiveness of the classifier. For example, if $\ln(P_T)$ is close to 0 (i.e., $P_T$ is close to 1), the classifier will react very quickly to changes. If $\ln(P_T)$ is set to more negative values, the classifier will react more slowly. By experimentation, $\ln(P_T) = -50$ turns out to be a good value.

Using the exemplar data, the determined log probability score for the first frame of the determined running state is $-3.84$, so the scaling adjustment factor is $50/3.84 = 13.02$. The first frame of the walk state is $-5.54$, so $\ln P(\text{walk})$ gets scaled with the scaling adjustment factor to $-5.54 * 13.02 = -72.13$.

Zero Probabilities Issue.

In one embodiment, probabilities in the model distributions are not allowed to be zero. Any probability below 1E-5 is replaced by 1E-5. In terms of logs, this convention means that no $\ln(P(c))$ can be below $-11.51$.

Movement State Model Conflict Resolution.

For most movement states, the statistical and rule-based models are equally robust in identifying the movement state and both are superior to the library comparison model. In some instances, however, the movement state determined by microprocessor 403 varies depending on the model used (i.e., for the same data, a movement state determined using the statistical model is not the same as the movement state determined using the rule-based model). In these instances, microprocessor 403 defaults to a conflict resolution protocol.

Conflict resolution between statistical model determinations and rule-based model determinations depends on the user's movement state. For example, because sitting and standing signatures look similar (i.e., accelerometer readings for sitting and standing without moving are substantially the same), the statistical model is not ideal for determining the difference between sitting and standing states. Thus, for sitting or standing movement states, the rule-based model is typically used to identify transitions between sitting and standing states (as discussed elsewhere herein) and those determinations typically override the results of the statistical state recognition accordingly. For the other movement states (e.g., lying, walking and running), statistical model determinations of the user's movement state are given priority over the rule-based model determinations of the user's movement state.

Posture Quality Determination

Once microprocessor 403 has determined a user's movement state by using one or more of the models (library comparison model, rule-based model, tilt angle model, and/or statistical model), microprocessor 403 determines the user's posture quality.

Microprocessor 403 uses accelerometer data to determine a user's posture quality (i.e., how well the user is balanced within a movement state, e.g., whether and how well the user's posture matches a desirable "good posture" for the determined movement state) over time. Microprocessor 403 makes this determination based on an average pelvic tilt angle (relative to the ground) derived from accelerometer data sampled over time (e.g., 750 times over 25 seconds). The tilt angle is measured, as is known, by calculating an angle between a sensing axis and the gravity vector. See, e.g., M. Clifford & L. Gomez (2005), "Measuring Tilt with Low-g Accelerometers", in *Freescale Semiconductor* (Application Note). An average tilt angle can be determined at any point after the accelerometer data have been normalized. Once the average pelvic tilt angle has been calculated, microprocessor 403 stores the average pelvic tilt angle with a time stamp in memory. An updated pelvic tilt angle is calculated at established time intervals when a user remains in a determined movement state and/or after the user transitions to a new movement state.

Figure 1:
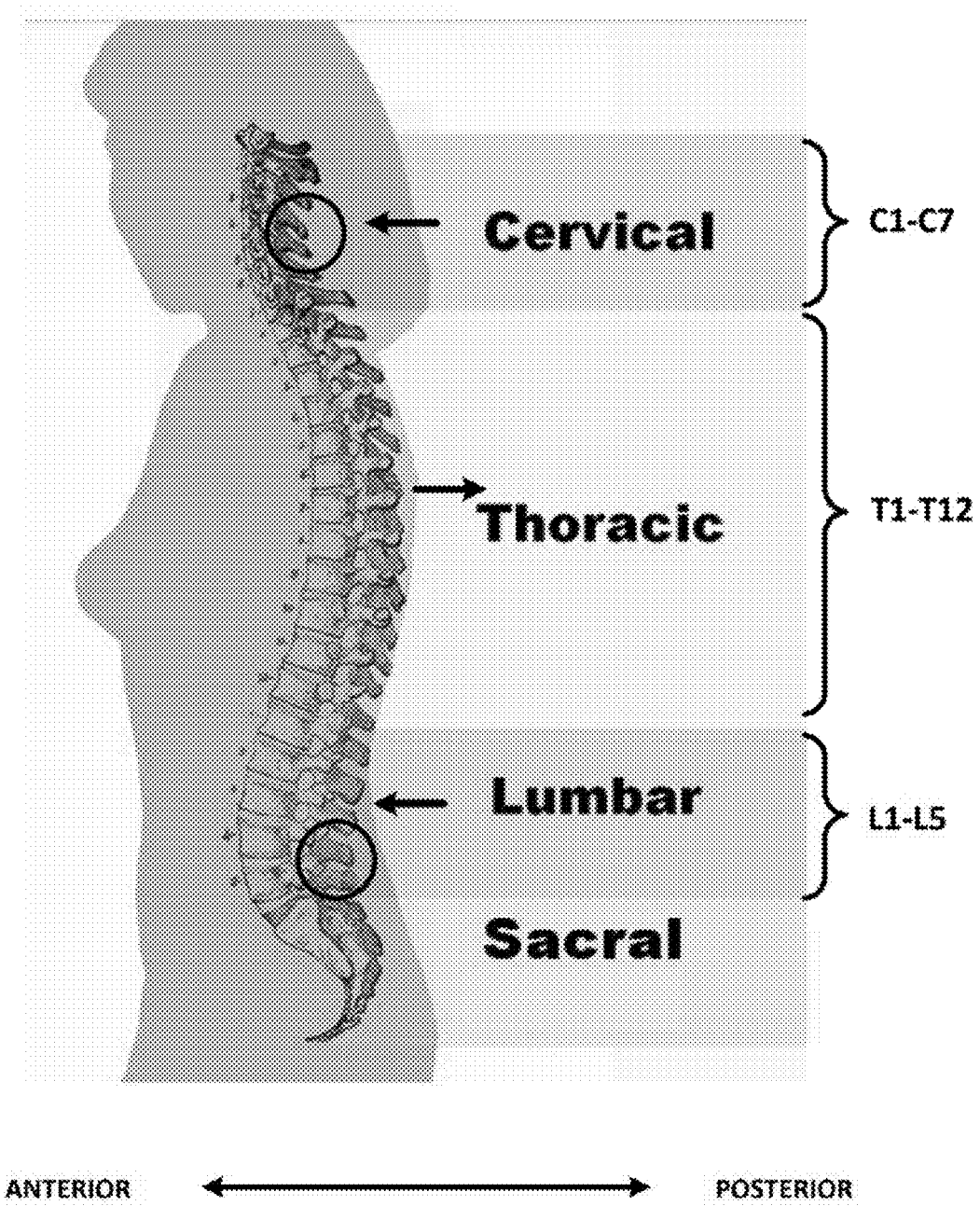
FIG. 1 is a diagram illustrating curvature in cervical, thoracic, and lumbar regions of a human spine.
Figure 2:
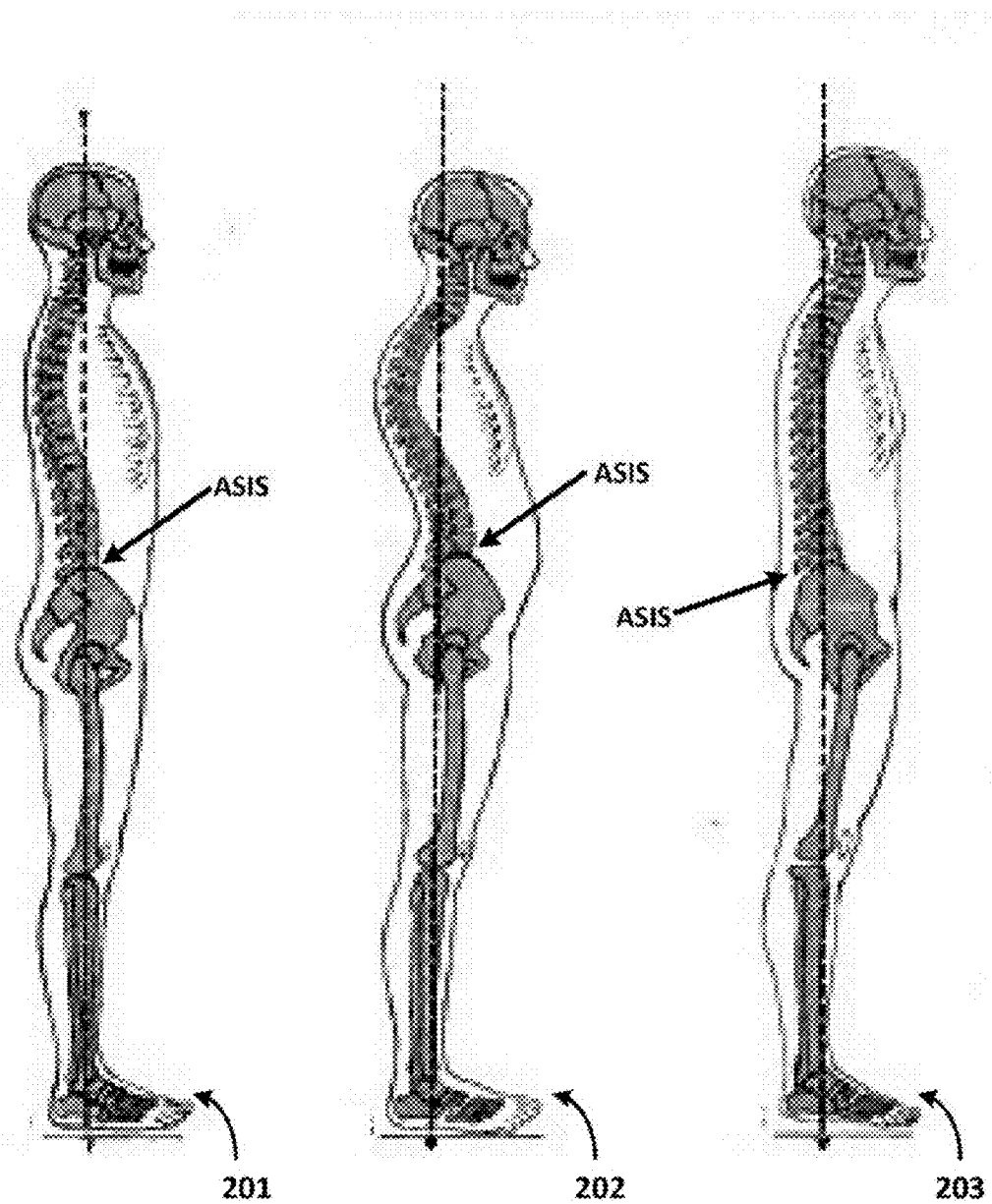
FIG. 2 is a set of diagrams illustrating good posture and poor posture.

Referring again to FIG. 2, good posture (shown in diagram 201) is defined as a posture with a neutral spine and a slightly anteverted pelvis such that the tip of the pelvis is tilted slightly forward. When the pelvis is slightly anteverted, the vertebrae stack up on each other and carry the weight of the body. An overly anteverted pelvis (shown in diagram 202) can cause an over-extension of the lumbar spine with consequent back health issues. When the pelvis is retroverted (tip of the pelvis is tilted back) the spine puts pressure on the lower back muscles to carry the weight of the upper back. An overly retroverted pelvis (shown in diagram 203) causes flexion in the lumbar spine which also can lead to back health issues.

A scale of good posture is determined by the tilt angle of the pelvis. Different body types may yield slightly different pelvic tilt angle readings, but correct calibration of accelerometer 405 when sensor device 301 is attached alleviates this issue. Good posture is benchmarked off of each individual user's average pelvic angle captured when walking.

When the user is standing with sensor device 301 attached at or around L4-L5 vertebrae, good posture is defined by a pelvic tilt angle reading of +/−5° compared to the average pelvic tilt angle captured while walking. At these angles, the pelvis is in a neutral position, on average. When the pelvis rotates backwards into a retroverted position such that the lumbar spine is flexed, the tilt angle increases beyond 5° greater than the average pelvic angle captured while walking. When the pelvis rotates forward into an overly anteverted position, the tilt angle decreases beyond 5° below the average pelvic angle captured while walking. Thus, poor posture is defined by pelvic tilt angles less than or greater than 5° of the average pelvic angle captured while walking. When the user is sitting, good posture is defined as a pelvic tilt angle of +/−10° of the average pelvic angle captured while walking. Poor sitting posture is defined as a pelvic tilt angle greater than +/−10° of the average pelvic angle captured while walking.

When the user is standing with sensor device 301 attached at or around S1-S2 vertebrae, good posture is also defined by a pelvic tilt angle reading of, e.g., +/−5° of the average pelvic angle captured while walking, with respect to the ground. At these angles, the pelvis is, on average, in a neutral position. When the pelvis rotates backwards into a retroverted position such that the lumbar spine is flexed, the tilt angle increases beyond the 5° of the average pelvic tilt angle captured while walking. When the pelvis rotates forward into an overly anteverted position, the tilt angle decreases beyond 5° below the average pelvic tilt angle while walking. Thus, poor posture is defined by pelvic tilt angles of less than or greater than, e.g., 5° of the average pelvic tilt angle captured while walking. When the user is sitting, good posture is defined as a pelvic tilt angle of, e.g., +/−10° of the average pelvic tilt angle while walking. Poor sitting posture is defined as a pelvic tilt angle of less than or greater than, e.g., 10° of the average pelvic tilt angle while walking.

If the average pelvic tilt angle while walking does not give an accurate enough determination of the user's good sitting and/or standing posture, then the user can start a self-calibration process. This entails watching an educational video, followed by a self-calibration for the sitting and standing postures using computing device 303. Self-calibration using a computing device involves getting into a good seated or standing position, beginning the calibration process on computing device 303, and holding the good posture for several moments while sensor device 301 averages the positional data of the good postural position. This process is used for either or both sitting and standing positions.

Biofeedback Based on User's Postural Description

Postural feedback is provided to the user in real-time via actuator 406, and/or through an application running on computing device 303. Postural feedback provided through the application running on computing device 303 can be provided in real-time, or a later time when computing device 303 is synchronized with sensor device 301.

In one embodiment, an animated graphic in the application running on computing device 303 is used to convey postural feedback to the user. The animated graphic is an avatar, an abstracted real-time animated character that reflects the movement and posture of the user in real-time. If the user sits with good posture, the avatar sits with good posture. If the user slouches, the avatar slouches. When the user stands up, the avatar stands up. When a user begins walking, the avatar walks. When the user runs, the avatar runs. When the user lies down, the avatar also lies down.

Figure 14:
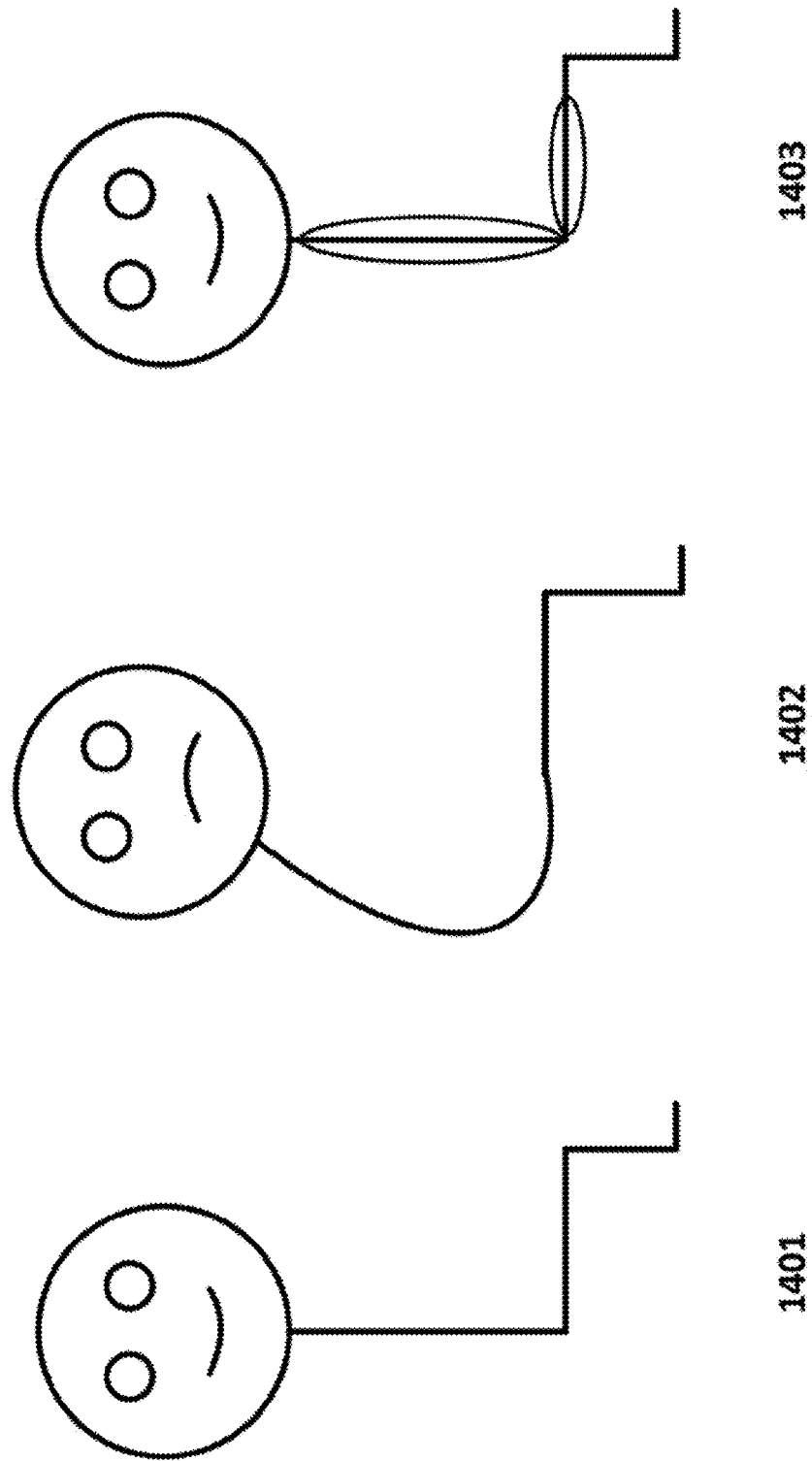
FIG. 14 is a graphical display of exemplary avatars used to provide postural feedback through a computing device to a user.

In a further embodiment indicating the user's posture, the avatar displays emotive feedback by, for example, assuming facial expressions and colors associated with good or bad posture. As an example shown in FIG. 14, when the user has good posture in a movement state (e.g., standing upright with good posture or sitting with good posture), avatar 1401 mimics the good posture in that movement state (e.g., while standing or sitting) as well, and couples the good posture with a smile on his face and a green body (not shown) to symbolize correct ("good") posture. When the user has poor posture in a movement state (e.g., slouches while sitting), avatar 1402 likewise displays poor posture in that movement state (e.g., slouches while sitting), and couples the poor posture with a less happy face and an orange body (not shown) as a warning that posture is not optimal. Over time, as a user improves his posture and movement, the avatar's appearance improves (e.g., larger muscles, certain clothing) to tangibly display the user's improvement. As an example, as a user's posture improves, avatar 1403 begins to have larger muscles and/or wears more attractive clothing or accessories (e.g., a crown).

This graphical display of information has many uses beyond relaying data. For instance, the avatar can be used to communicate with other friends and family also using a sensor device 301, thereby facilitating interpersonal communication, goal tracking, and games. For example, multiple users can share their avatars with each other and view all of the avatars on display screens of their respective computing devices 303. Games and challenges can also be facilitated through this new experience. For example, users can challenge each other to a posture game in which each user aspires to have the best posture for a specific amount of time. Each user's corresponding avatar will reflect his progress towards this challenge in real-time on the other users' computing devices. Users can also cooperatively help each other with goal-oriented games, as certain gestures may enable the avatars to navigate through mazes or capture a certain number of objects with the aim of attaining a certain goal. In addition, this visualization of another user's avatar as well as one's own avatar allows for friends and family to interact with each other through virtual real-time visualization, thereby allowing the users to comment on biomechanics of the other users' postures in real-time.

Communication of user data and user avatars to other users is accomplished by transmitting movement state and posture quality to computing devices 303 via wireless communication module 404 and cloud server 305. The application running on a first user's computing device 303 interprets the movement state and posture quality incoming from a second user's computing device 303 via cloud server 305 as a specific position and animates an avatar representing the second user based on new position data points.

Customization of Sensor Device

The user can control sensor device settings (e.g., sensory feedback settings) through the application running on computing device 303. For example, a user can activate calibration of personalized posture and movement, can change actuator settings such duration and/or intensity of feedback actuation (e.g., duration and/or intensity of vibration) and/or duration of in a poor posture before feedback is triggered, or turn off sensory feedback.

If the user activates calibration of personalized posture and movement, the user can record a series of personalized stationary postures, pelvic tilt angles, and/or state transition signals for later use in quantifying good and bad posture. Recorded personalized state transitions are stored in the movement library and used for comparison against live acceleration data to better detect various movement transitions.

In addition, the sensitivity to trigger biofeedback can change over time given the user's improvement in posture. For example, as a higher percentage of correct posture positions are detected for the user over time, time to trigger the biofeedback can decrease (i.e., there is a quicker trigger of the vibratory feedback as a user's performance improves).

When the user desires to change sensor device settings or calibrations, these changes are transmitted via wireless communication module 404 to sensor device 301 and stored within memory in microprocessor 403 until or unless changed again.

Behavioral patterns analyzed from user data in cloud server 305 can also be used to calibrate sensor device settings and performance. For example, responses to biofeedback can be analyzed. If the user does not respond readily to feedback, the system can increase the feedback actuation intensity or decrease the feedback frequency. For example, after behavioral analysis in cloud server 305, a command can be sent to computing device 303 to change sensor device settings. In addition, user data can be stored in cloud server 305 can be used to tailor the statistical model and/or the rule-based model, as well as the biofeedback model to that user.

Finally, personalized recommendations such as tips, exercises, stretches, and goal settings, can be provided to the user based on behavior analysis of the user's behavior over time. Behavior analysis can consist of reviewing and combining the user's personal movement data, the user's history of reaction to biofeedback, and/or the user's usage patterns and desire to change the settings of the real time biofeedback and other settings.

The user may have a personal data hub on cloud server 305 which can contain summarized data of user's posture, goals and activity breakdown available for viewing on computing device 303. Movement and behavior patterns of the user are analyzed in cloud server 305 to help personalize behavior of sensor device 301 and to tailor behavioral recommendations to the user. For example, various movements, exercises, and stretches may be analyzed to find correlations with the increase or decrease of back pain as discussed elsewhere herein.

In addition to using the user's personal data to provide feedback to that user, personal data from multiple users can be combined for analysis in cloud server 305 and used to provide feedback. For example, data in cloud server 305 can be mined to study movements correlated to increasing or decreasing lower back pain. Such an analysis can yield new personalized regimens and treatments for managing back pain in different population groups. As another example, movement signatures of people with varying degrees of symptomatology (e.g., severe, moderate, and mild back pain) can be analyzed demographically. Correlations of data from users based on demographics, movement, and/or symptoms can be used to provide personalized improvement plans and/or actionable goals that may lead to alleviation of back pain, increased confidence, and a quicker method to more toned core muscles. Such personalized plans can be automatically implemented by the sensor itself, or can be controlled by the user such that the user can implement portions of the plan as desired. Behavioral data (e.g., responses to biofeedback actuations) can also be analyzed to personalize sensor device behavior so as to provide feedback to the user during optimal instances in which the user may be more motivated or open to adjusting posture position.

The disclosed method and apparatus has been explained above with reference to several embodiments. Other embodiments will be apparent to those skilled in the art in light of this disclosure. Certain aspects of the described method and apparatus may readily be implemented using configurations other than those described in the embodiments above, or in conjunction with elements other than those described above. For example, although embodiments of the sensor device described herein discuss placement of the sensor device on the back, the sensor device can be placed on other parts of the body (e.g., neck) as well as on various equipment such as chairs, golf clubs, tennis racquets, etc.

Further, it should also be appreciated that the described method and apparatus can be implemented in numerous ways, including as a process, an apparatus, or a system. The methods described herein may be implemented by program instructions for instructing a processor to perform such methods, and such instructions recorded on a computer readable storage medium such as a hard disk drive, floppy disk, optical disc such as a compact disc (CD) or digital versatile disc (DVD), flash memory, etc., or a computer network wherein the program instructions are sent over optical or electronic communication links. It should be noted that the order of the steps of the methods described herein may be altered and still be within the scope of the disclosure.

It is to be understood that the examples given are for illustrative purposes only and may be extended to other implementations and embodiments with different conventions and techniques. While a number of embodiments are described, there is no intent to limit the disclosure to the embodiment(s) disclosed herein. On the contrary, the intent is to cover all alternatives, modifications, and equivalents apparent to those familiar with the art.

In the foregoing specification, the invention is described with reference to specific embodiments thereof, but those skilled in the art will recognize that the invention is not limited thereto. Various features and aspects of the above-described invention may be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A method of providing postural feedback comprising:
   receiving by a microprocessor at repeated intervals data from a tri-axial accelerometer, the microprocessor and the tri-axial accelerometer comprising a sensor device attached to a user, the sensor device further comprising memory, an actuator, and a power source;
   normalizing by the microprocessor the received accelerometer data;
   determining by the microprocessor a postural description of the user based on the normalized received accelerometer data,
      wherein the postural description comprises a current movement state, and
      wherein determining the postural description based on the normalized received accelerometer data comprises:
         computing feature vectors for the normalized received accelerometer data;
         quantizing the feature vectors;
         assigning the feature vectors to Gaussian distributions,
         acquiring distribution histograms for multiple movement states; and
         comparing the distribution histograms to determine the current movement state from the multiple movement states;
   and
   triggering by the microprocessor the actuator to output sensory feedback based on the postural description of the user.

2. The method of claim 1 further comprising transmitting across a wireless electronic communication connection to a computing device the postural description of the user and the normalized received accelerometer data.

3. A postural feedback apparatus comprising:
   a sensor device configured to be attached on a user, the sensor device comprising:
      a tri-axial accelerometer;
      an actuator; and
      a microprocessor configured to
         receive data from the tri-axial accelerometer about movement of the user;
         normalize the received accelerometer data;
         determine a postural description of the user based on the normalized received accelerometer data,
            wherein the postural description comprises a current movement state, and
            wherein the microprocessor configured to determine the postural description of the user based on the normalized received accelerometer data comprises the microprocessor configured to:
               compute feature vectors for the normalized received accelerometer data;
               quantize the feature vectors;
               assign the feature vectors to Gaussian distributions;
               acquire estimated distribution histograms for multiple movement states; and
               compare the distribution histograms to determine the current movement state from the multiple movement states:
         and
         trigger the actuator to output sensory feedback based on the postural description of the user.

4. The apparatus of claim 3 wherein the sensor device further comprises a wireless communication module.

5. The apparatus of claim 4 wherein the microprocessor is further configured to communicate with the wireless communication module to transmit the postural description of the user and the normalized received accelerometer data to a computing device.

6. A non-transitory computer readable medium having stored thereupon computing instructions comprising:
   a code segment to receive by a microprocessor at repeated intervals data from a tri-axial accelerometer, the microprocessor and the tri-axial accelerometer comprising a sensor device attached to a user, the sensor device further comprising memory, an actuator, and a power source;
   a code segment to normalize by the microprocessor the received accelerometer data;
   a code segment to determine by the microprocessor a postural description of the user based on the normalized received accelerometer data;
   a code segment to trigger by the microprocessor the actuator to output sensory feedback based on the postural description of the user;
   a code segment to transmit from the microprocessor across an electronic communication connection to a computing device the postural description of the user to be displayed on the computing device as an avatar with an appearance, the appearance of the avatar representing the postural description of the user; and
   a code segment to transmit from the computing device across a network connection to a cloud server the postural description of the user, the cloud server using the postural description of the user to tailor biofeedback for the user.

* * * * *